US009295676B2

(12) United States Patent
Berezov et al.

(10) Patent No.: US 9,295,676 B2
(45) Date of Patent: Mar. 29, 2016

(54) MUTATION MIMICKING COMPOUNDS THAT BIND TO THE KINASE DOMAIN OF EGFR

(75) Inventors: Alan Berezov, West Hollywood, CA (US); Mark I. Greene, Penn Valley, PA (US); Natalie Minkovsky, Philadephia, PA (US); Zheng Cai, Wynnewood, PA (US); Hongtao Zhang, Paoli, PA (US)

(73) Assignee: The Trustees Of The University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/005,069

(22) PCT Filed: Mar. 16, 2012

(86) PCT No.: PCT/US2012/029386
§ 371 (c)(1),
(2), (4) Date: Jan. 2, 2014

(87) PCT Pub. No.: WO2012/125904
PCT Pub. Date: Sep. 20, 2012

(65) Prior Publication Data
US 2014/0135298 A1 May 15, 2014

Related U.S. Application Data

(60) Provisional application No. 61/453,626, filed on Mar. 17, 2011, provisional application No. 61/454,083, filed on Mar. 18, 2011.

(51) Int. Cl.
| | |
|---|---|
| A61K 31/573 | (2006.01) |
| A61K 31/4525 | (2006.01) |
| A61K 31/44 | (2006.01) |
| A61K 31/505 | (2006.01) |
| A61K 31/4184 | (2006.01) |
| A61K 31/4418 | (2006.01) |
| A61K 31/517 | (2006.01) |
| A61K 31/635 | (2006.01) |
| A61K 45/06 | (2006.01) |
| A61K 31/57 | (2006.01) |
| C07D 213/76 | (2006.01) |
| C07D 239/42 | (2006.01) |
| C07D 405/04 | (2006.01) |
| C07D 405/06 | (2006.01) |
| C07J 7/00 | (2006.01) |

(52) U.S. Cl.
CPC .......... *A61K 31/573* (2013.01); *A61K 31/4184* (2013.01); *A61K 31/44* (2013.01); *A61K 31/4418* (2013.01); *A61K 31/4525* (2013.01); *A61K 31/505* (2013.01); *A61K 31/517* (2013.01); *A61K 31/57* (2013.01); *A61K 31/635* (2013.01); *A61K 45/06* (2013.01); *C07D 213/76* (2013.01); *C07D 239/42* (2013.01); *C07D 405/04* (2013.01); *C07D 405/06* (2013.01); *C07J 7/008* (2013.01)

(58) Field of Classification Search
USPC ......... 514/171, 179, 235.8, 266.24, 275, 320, 514/349; 548/305.1; 544/332
See application file for complete search history.

(56) References Cited

U.S. PATENT DOCUMENTS

| | | |
|---|---|---|
| 5,457,105 A | 10/1995 | Barker |
| 5,616,582 A | 4/1997 | Barker |
| 5,747,498 A | 5/1998 | Schnur et al. |
| 5,770,599 A | 6/1998 | Gibson |
| 6,251,912 B1 | 6/2001 | Wissner et al. |
| 6,391,874 B1 | 5/2002 | Cockerill et al. |
| 6,713,485 B2 | 3/2004 | Carter |
| 6,727,256 B1 | 4/2004 | Carter et al. |
| 6,828,320 B2 | 12/2004 | Cockerill et al. |
| 6,900,221 B1 | 5/2005 | Norris |
| 7,087,613 B2 | 8/2006 | Raggon et al. |
| 7,157,466 B2 | 1/2007 | McClure et al. |
| 7,547,781 B2 | 6/2009 | Qian et al. |
| 7,585,859 B2 | 9/2009 | Ibrahim et al. |
| RE41,065 E | 12/2009 | Schnur |
| 7,846,938 B2 | 12/2010 | Cai et al. |
| 2005/0084905 A1 | 4/2005 | Prescott et al. |
| 2007/0123537 A1 | 5/2007 | Herget |
| 2008/0004297 A1 | 1/2008 | Cai et al. |
| 2008/0139590 A1 | 6/2008 | Qian et al. |
| 2008/0194578 A1 | 8/2008 | Qian et al. |
| 2008/0221132 A1 | 9/2008 | Cai et al. |
| 2009/0076022 A1 | 3/2009 | Cai et al. |
| 2009/0111772 A1 | 4/2009 | Cai et al. |
| 2009/0209758 A1 | 8/2009 | Qian et al. |

(Continued)

FOREIGN PATENT DOCUMENTS

| | | |
|---|---|---|
| EP | 0068553 * | 6/1982 |
| WO | WO 2012/125904 A1 | 9/2012 |
| WO | WO 2012/125913 A1 | 9/2012 |

OTHER PUBLICATIONS

Thatcher et al. The Oncologist 2009; 14:840-847.*
Boland (Ann Rheum Dis 1953 12: 125-128 ).*
Ranson et al (Cancer Chemother Pharmacol (2010) 66:53-58).*
Berge, "Pharmaceutical Salts", Journal of Pharmaceutical Sciences, Jan. 1977, 66(1):1-19.
Choi et al, "EGF-Independent Activation of Cell-Surface Egf Receptors Harboring Mutations Found in Gefitinib-Sensitive Lung Cancer", Oncogene, 2007, 26, 1567-1576.
Ewing, "DOCK 4.0: Search Strategies for Automated Molecular Docking of Flexible Molecule databases", Journal of Computer-Aided Molecular Design, 2001, 15: 411-428.
Fabian et al, "A Small Molecule-Kinase Interaction Map for Clinical Kinase Inhibitors", Nature Biotechnology, Mar. 2005, 23(3), 329-336.
Fingl et al, "The Pharmacological Basis of Therapeutics", Fourth Edition, 1975, 1(1), The Macmillan Company, New York, NY 10022, 6 pages.
Heymann et al, "The T790M "Gatekeeper"Mutation in EGFR Mediates Resistance to Low Concentrations of an Irreversible EGFR Inhibitor", Mol. Cancer Ther., Apr. 2008;7:874-879.

(Continued)

*Primary Examiner* — Shirley V Gembeh
(74) *Attorney, Agent, or Firm* — Baker & Hostetler LLP

(57) ABSTRACT

This invention is in the fields of cancer therapy. More particularly it concerns compounds which are useful agents for treating cell proliferative disorders, especially those disorders characterized by over activity and/or inappropriate activity of a EGFR, including EGFR-related cancers, particularly for expanding the efficacy of drugs previously developed for this purpose, and for methods of treatments using the compounds for this purpose.

27 Claims, 19 Drawing Sheets

(56) References Cited

U.S. PATENT DOCUMENTS

2009/0306101 A1 12/2009 Solca et al.
2009/0318480 A1 12/2009 Solca

OTHER PUBLICATIONS

International Patent Application No. PCT/US12/29386: International Search Report and the Written Opinion dated Jun. 29, 2012, 10 pages.
International Patent Appln. No. PCT/US2012/029410: International Preliminary Report dated Sep. 26, 2013, 7 pages.
International Patent Appln. No. PCT/US2012/029410: International Search Report and the Written Opinion dated Jul. 5, 2012, 11 Pages.
Jackman, "Impact of Epidermal Growth Factor Receptor and KRAS Mutations on Clinical Outcomes in Previously Untreated Non-Small Cell Lung Cancer Patients: Results of an Online Tumor Registry of Clinical Trials", Clinical Cancer Research, Aug. 2009, 15(16):5267-5273.
Kotra et al, "Homology Models of the Mutated EGFR and Their Response Towards Quinazolin Analogues", Journal of Molecular Graphics and Modelling, 2008, 27, 244-254.
Kwak et al, "Irreversible Inhibitors of the EGF Receptor May Circumvent Acquired resistance to Gefitinib", PNAS, May 24, 2005, 102(21), 7665-7670.
Lynch et al, "Activating Mutations in the Edpidermal Growth Factor Receptor Underlying Responsiveness of Non-Small Cell Lung Cancer to Gefitinib", N. Engl. J. Med., May 2004, 350, 2129-2139.
Minna et al, "A Bull's Eye for Targeted Lung Cancer Therapy", Science, Jun. 4, 2004, 304, 1458-1461.
Paez et al, "EGFR Mutations in Lung Cancer: Correlation with Clinical Response to Gefitinib Therapy", Science, Jun. 4, 2004, 304,1497-1500.
Sordella, "Gefitinib-Sensitizing EGFR Mutations in Lung Cancer Activate Anti-Apoptotic Pathways", Science, Aug. 20, 2004, 1163-1167.
Vikis et al, "EGFR-T790M is a Rare Ling Cancer Susceptibility Allele with Enhanced Kinase Activity", Cancer Research, May 2007, 67:4665-4670.
Wakeling et al, "Specific Inhibition of Epidermal Growth Factor Receptor Tyrosine Kinase by 4-anilinoquinazolines", Breast Cancer Research and Treatment, 1996, 38:67-73.
Yu et al, "Resistance to an Irreversible Epidermal Growth Factor Receptor (EGFR) Inhibitor in EGFR-Mutant Lung Cancer Reveals Novel Treatment Strategies", Cancer Research, Nov. 1, 2007, 67:10417-10427.
Yun et al, "Structures of Lung Cancer-Derived EGFR Mutants and Inhibitor Complexes: Mechanism of Activation and Insights Into Differential Inhibitor Sensitivity", Cancer Cell., Mar. 2007; 11(3): 217-227.
Sambasiva, et al., "Structure Activity Relationship of Corticosteroids", NIPER, accessed Oct. 26, 2015, 30 pgs.

* cited by examiner

EGFR - Tarceva

EGFR - Tarceva + EEO3

EGFR - Tarceva

EGFR - Tarceva + EEO4

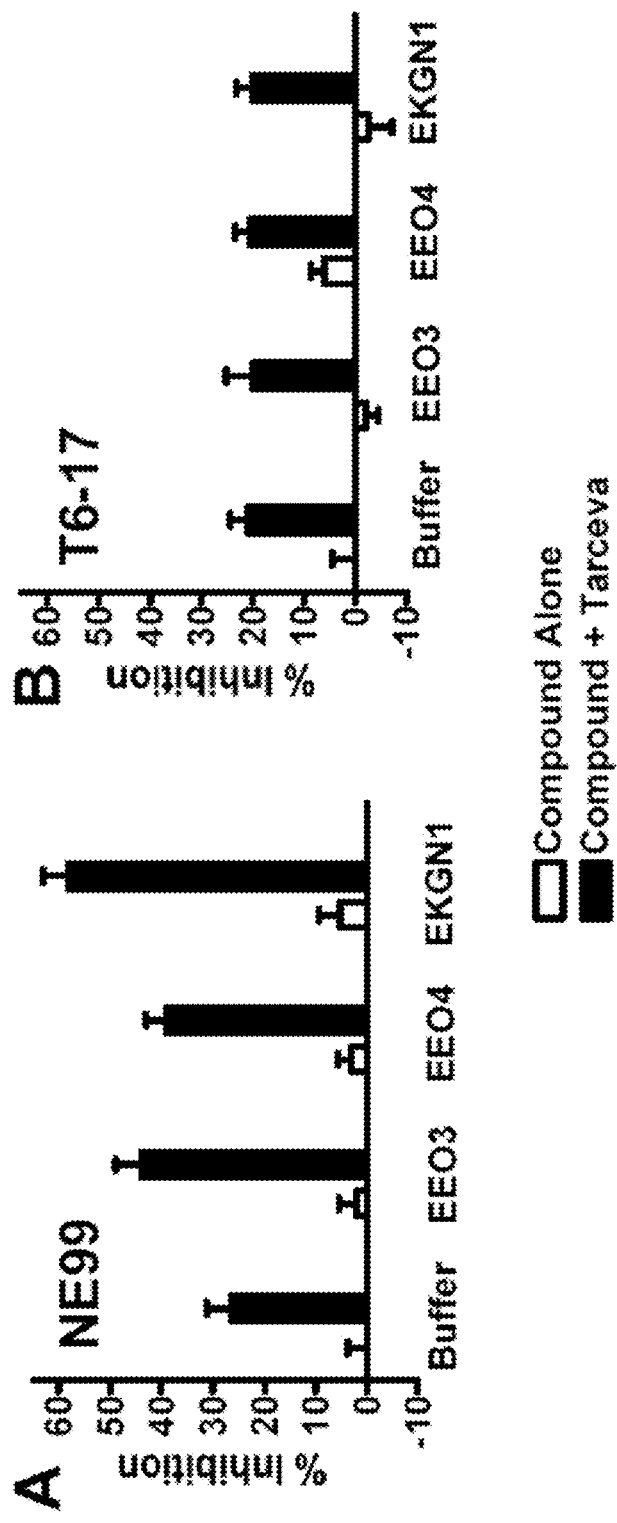
FIG. 4A/B

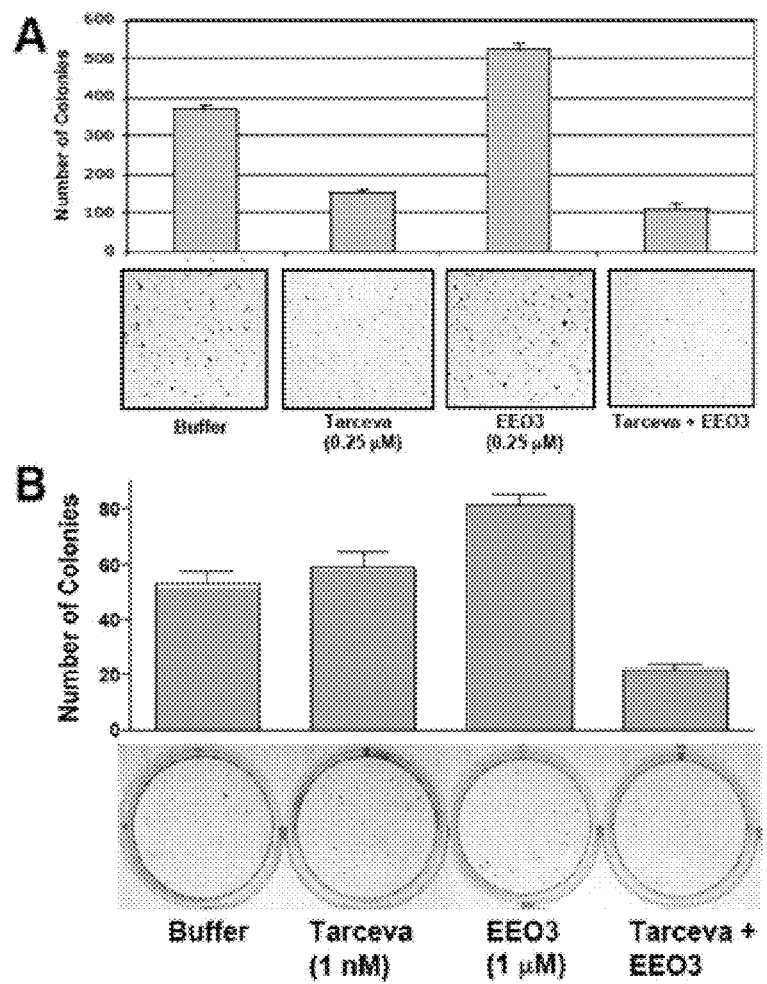

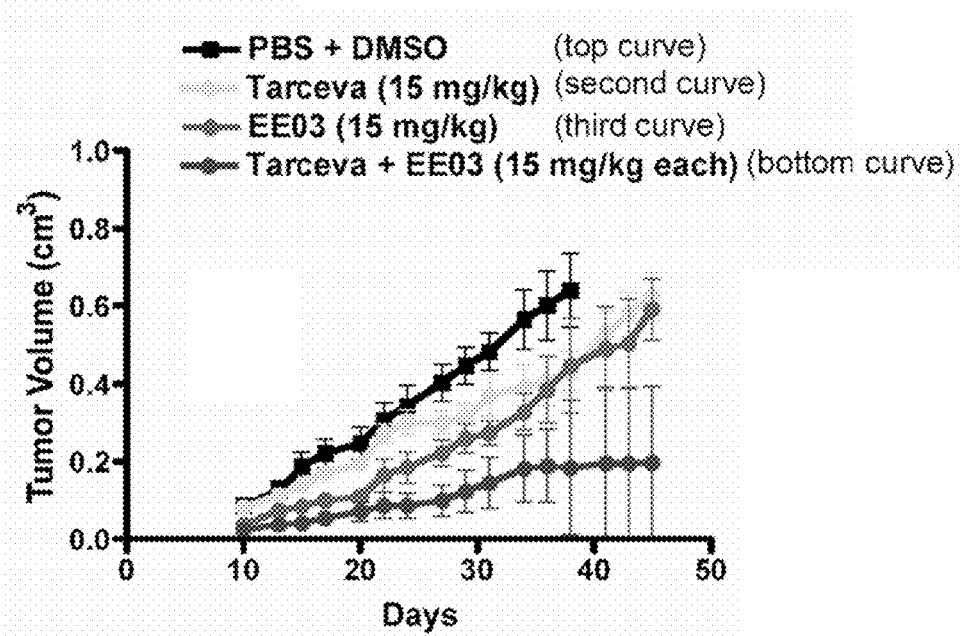

FIG. 12

Human EGFR Kinase domain

```
                                                    AGT GGA GAA GCT CCC AAC
                                                    ser gly glu ala pro asn
2347/701                                2377/711
CAA GCT CTC TTG AGG ATC TTG AAG GAA ACT GAA TTC AAA AAG ATC AAA GTG CTG GGC TCC
gln ala leu leu arg ile leu lys glu thr glu phe lys lys ile lys val leu gly ser
2407/721                                2437/731
GGT GCG TTC GGC ACG GTG TAT AAG GGA CTC TGG ATC CCA GAA GGT GAG AAA GTT AAA ATT
gly ala phe gly thr val tyr lys gly leu trp ile pro glu gly glu lys val lys ile
2467/741                                2497/751
CCC GTC GCT ATC AAG GAA TTA AGA GAA GCA ACA TCT CCG AAA GCC AAC AAG GAA ATC CTC
pro val ala ile lys glu leu arg glu ala thr ser pro lys ala asn lys glu ile leu
2527/761                                2557/771
GAT GAA GCC TAC GTG ATG GCC AGC GTG GAC AAC CCC CAC GTG TGC CGC CTG CTG GGC ATC
asp glu ala tyr val met ala ser val asp asn pro his val cys arg leu leu gly ile
2587/781                                2617/791
TGC CTC ACC TCC ACC GTG CAG CTC ATC ACG CAG CTC ATG CCC TTC GGC TGC CTC CTG GAC
cys leu thr ser thr val gln leu ile thr gln leu met pro phe gly cys leu leu asp
2647/801                                2677/811
TAT GTC CGG GAA CAC AAA GAC AAT ATT GGC TCC CAG TAC CTG CTC AAC TGG TGT GTG CAG
tyr val arg glu his lys asp asn ile gly ser gln tyr leu leu asn trp cys val gln
2707/821                                2737/831
ATC GCA AAG GGC ATG AAC TAC TTG GAG GAC CGT CGC TTG GTG CAC CGC GAC CTG GCA GCC
ile ala lys gly met asn tyr leu glu asp arg arg leu val his arg asp leu ala ala
2767/841                                2797/851
AGG AAC GTA CTG GTG AAA ACA CCG CAG CAT GTC AAG ATC ACA GAT TTT GGG CTG GCC AAA
arg asn val leu val lys thr pro gln his val lys ile thr asp phe gly leu ala lys
2827/861                                2857/871
CTG CTG GGT GCG GAA GAG AAA GAA TAC CAT GCA GAA GGA GGC AAA GTG CCT ATC AAG TGG
leu leu gly ala glu glu lys glu tyr his ala glu gly gly lys val pro ile lys trp
2887/881                                2917/891
ATG GCA TTG GAA TCA ATT TTA CAC AGA ATC TAT ACC CAC CAG AGT GAT GTC TGG AGC TAC
met ala leu glu ser ile leu his arg ile tyr thr his gln ser asp val trp ser tyr
2947/901                                2977/911
GGG GTG ACC GTT TGG GAG TTG ATG ACC TTT GGA TCC AAG CCA TAT GAC GGA ATC CCT GCC
gly val thr val trp glu leu met thr phe gly ser lys pro tyr asp gly ile pro ala
3007/921                                3037/931
AGC GAG ATC TCC TCC ATC CTG GAG AAA GGA GAA CGC CTC CCT CAG CCA CCC ATA TGT ACC
ser glu ile ser ser ile leu glu lys gly glu arg leu pro gln pro pro ile cys thr
3067/941                                3097/951
ATC GAT GTC TAC ATG ATC ATG GTC AAG TGC TGG ATG ATA GAC GCA GAT AGT CGC CCA AAG
ile asp val tyr met ile met val lys cys trp met ile asp ala asp ser arg pro lys
3127/961                                3157/971
TTC CGT GAG TTG ATC ATC GAA TTC TCC AAA ATG GCC CGA GAC CCC CAG CGC TAC CTT GTC
phe arg glu leu ile ile glu phe ser lys met ala arg asp pro gln arg tyr leu val
3187/981                                3217/991
ATT CAG GGG GAT GAA AGA ATG CAT TTG CCA AGT CCT ACA GAC TCC AAC TTC TAC CGT GCC
ile gln gly asp glu arg met his leu pro ser pro thr asp ser asn phe tyr arg ala
3247/1001                               3277/1011
CTG ATG GAT GAA GAA GAC ATG GAC GAC GTG GTG GAT GCC GAC GAG TAC CTC ATC CCA CAG
leu met asp glu glu asp met asp asp val val asp ala asp glu tyr leu ile pro gln
3307/1021                               3337/1031
CAG GGC
gln gly
```

MUTATION MIMICKING COMPOUNDS THAT BIND TO THE KINASE DOMAIN OF EGFR

CROSS-REFERENCE TO RELATED APPLICATIONS

This application is the National Stage of International Application No. PCT/US2012/029386, filed Mar. 16, 2012, which claims the benefit of U.S. Provisional Application No. 61/453,626, filed Mar. 17, 2011, and U.S. Provisional Application No. 61/454,083, filed Mar. 18, 2011, the disclosures of which are incorporated herein by reference in their entireties.

GOVERNMENT RIGHTS

This invention was made with government support under Grant Nos. 5R01CA089481 and 5R01CA055306 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Mar. 14, 2012, is named UPN-5735.txt and is 11,005 bytes in size.

TECHNICAL FIELD

This invention relates to the fields of cancer therapy. More particularly it concerns compounds which are useful agents for treating cell proliferative disorders, especially those disorders characterized by over activity and/or inappropriate activity of an EGFR, including EGFR-related cancers, particularly for expanding the efficacy of drugs previously developed for this purpose, and for methods of treatments using the compounds for this purpose.

BACKGROUND

The erbB or EGFR family is a subclass of cell surface receptors with intrinsic tyrosine kinase activity known as receptor tyrosine kinases (RTKs). The EGFR family comprises four members: EGFR (also known as erbB1) itself, erbB2 (HER2/Neu), erbB3 and erbB4. EGFR plays a critical role in normal embryonic development and is also known to drive the growth of tumors.

As for most RTKs the first step in the activation of EGFR is ligand induced receptor dimerization. The intracellular kinase domains in the ligand-induced EGFR dimer become activated by autophosphorylation in trans. Subsequent phosphorylation on tyrosines in the regulatory C-terminal tail creates binding sites for the recruitment of multiple downstream signaling molecules via interactions with their SH2 domains.

Abberrant EGFR activation, resulting in EGFR overexpression (known as upregulation) or overactivity is strongly implicated in a cancers, including anal, breast, ovarian, head and neck, lung, pancreatic, and colorectal cancers and glioblastoma multiforme, and is already the target of several anti-cancer therapeutics. Mutations, amplifications or misregulations of EGFR or family members are implicated in about 30% of all epithelial cancers.

The identification of EGFR as an oncogene has led to the development of anticancer therapeutics directed against EGFR. Two major strategies have been used for suppressing aberrant EGFR signalling: antibody targeting of the receptor ectodomain and small molecule inhibition of the tyrosine kinase domain. The antibody approach provides high target specificity, but has limitations and challenges in drug development because of the protein nature of the therapeutic agent, including cost and delivery. Cetuximab and panitumumab are examples of monoclonal antibody inhibitors. Other monoclonals in clinical development are zalutumumab, nimotuzumab, and matuzumab. The monoclonal antibodies block the extracellular ligand binding domain. With the binding site blocked, signal molecules can no longer attach there and activate the tyrosine kinase.

Another method of inhibiting abberant EGFR signalling is to use small molecules to inhibit the EGFR tyrosine kinase, which is on the cytoplasmic side of the receptor. Without kinase activity, EGFR is unable to activate itself, which is a prerequisite for binding of downstream adaptor proteins. Ostensibly by halting the signaling cascade in cells that rely on this pathway for growth, tumor proliferation and migration is diminished. Gefitinib, erlotinib, and lapatinib (mixed EGFR and ERBB2 inhibitor) are examples of small molecule kinase inhibitors which function as competitive TKIs by reversibly binding to the ATP site on the EGFR kinase domain. See e.g., Lynch, et al., "Activating mutations in the epidermal growth factor receptor underlying responsiveness of non-small-cell lung cancer to gefitinib," *N. Engl. J Med.*, 350: 2129-39 (2004); Paez, et al., "EGFR mutations in lung cancer: correlation with clinical response to gefitinib therapy," Science, 304: 1497-1500 (2004), each of which is incorporated by reference in its entirety.

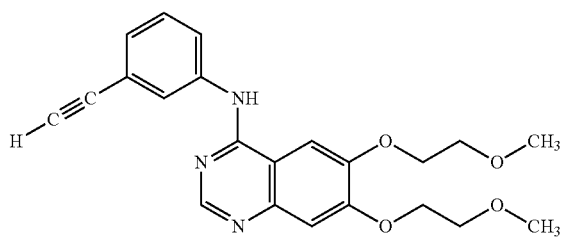

Erlotinib (Tarceva)

-continued

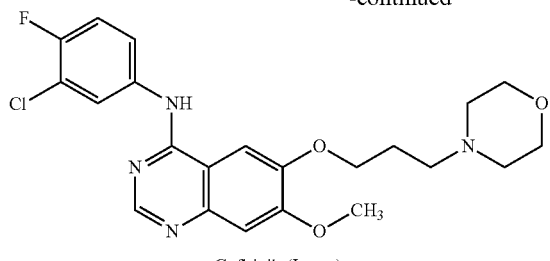
Gefitinib (Iressa)

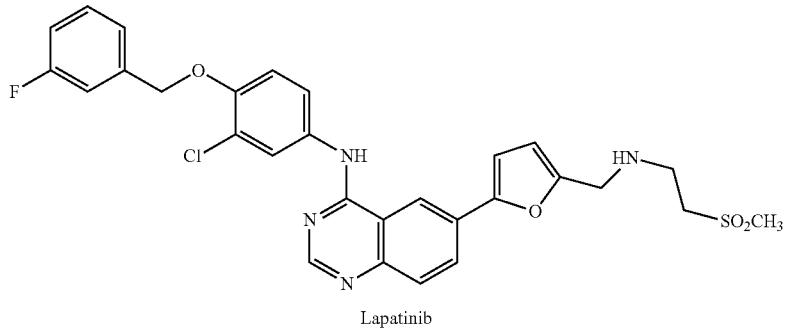
Lapatinib

The advantages of small-molecule drugs over therapeutic proteins include the ease of manufacturing and administration, the potential for oral dosing, low immunogenity and applicability to a wider range of disease targets, including those inside the cell. Indeed, small molecule inhibitors of the tyrosine kinase domain of EGFR (i.e., Iressa® and Tarceva®) have been successfully developed as drugs, which directly target the EGFR. But not all patients can benefit from such drugs. Patients can be been divided into EGFR positive and negative, based upon whether a tissue test shows a mutation. One of the most common mutation that sensitizes tumors to small molecule tyrosine kinase inhibitors is the so-called L858R mutation, wherein Leu-858 in the EGFR peptide sequence is replaced by an Arg-858 (so-called "L858R mutation"). EGFR positive patients have shown an impressive 60% response rate which exceeds the response rate for conventional chemotherapy. For example, see Jackman D M, et al., "Impact of epidermal growth factor receptor and KRAS mutations on clinical outcomes in previously untreated non-small cell lung cancer patients: results of an online tumor registry of clinical trials". *Clin. Cancer Res.* 15 (16): 5267-73 (August 2009). However, this mutation which allows for this success exists in only in a small sub-population (ca. 5%) of non-small cell lung cancer patients that harbor this particular mutation in the tyrosine kinase domain of EGFR. Minna, et al., "Cancer. A bull's eye for targeting lung cancer therapy," *Science*, 304: 1458-61 (2004), which is incorporated by reference herein in its entirety.

In the metastatic setting, EGFR mutations are strong predictors of efficacy for the EGFR tyrosine kinase inhibitors (TKIs), erlotinib (Tarceva®) and gefitinib (Iressa®). Patients whose tumors harbor EGFR L858R mutations display a >70% radiographic response rate in prospective trials, including randomized phase III trials. Compared to those with EGFR wild-type tumors, patients with EGFR mutant tumors display a longer progression-free survival on EGFR TKI therapy than those who receive chemotherapy. Patients with metastatic EGFR mutant tumors treated with 'first-generation' EGFR TKIs have a median survival of more than two years. Prolonged survival may also be due to the fact that patients with EGFR mutant tumors have a better prognosis in general compared to those with EGFR wild-type tumors. Patients with EGFR mutant tumors treated with an EGFR TKI in the first-line setting may live longer than those treated in the second-line setting (30.5 months vs. 23.6 months, p=0.31).

There is a need for small molecule pharmaceuticals which regulate the overexpression of EGFR so as to inhibit cell proliferative disorders characterized by over-activity and/or inappropriate activity of EGFR in a wider population of patients suffering from such disorders, including EGFR-related cancers.

SUMMARY

The present disclosure provides small molecule compounds capable of mimicking the effects produced by the drug-sensitizing kinase domain mutations known to occur in kinase domain of the epidermal growth factor receptor (EGFR). Without intending to be bound by any particular theory, it may be that these small molecules affect the kinase domain of EGFR so as to alter the signaling properties of the EGF receptor, make EGFR expressing tumor cells more EGFR dependent and thus sensitize these tumor cells to inhibition with the traditional TKI inhibitors. As such, the small molecules of the present invention can have the effect of improving the reach and efficacy of traditional EGFR and/or Src tyrosine kinase inhibitors (TKIs).

Certain embodiments of the present invention provide pharmaceutical compositions comprising a compound capable of mimicking the L858R mutation in the tyrosine kinase domain of the epidermal growth factor receptor (EGFR) in an amount effective to mimic the mutation. Additional embodiments of these compositions characterized these compounds using exemplary structures, binding affinities, and using biological and other test data. Use of these compounds in the preparation of such compositions or medicaments is also considered.

Other embodiments further provide that these pharmaceutical compositions comprise an EGFR tyrosine kinase inhibitor in an amount effective to inhibit a cell proliferative disorder characterized by over-activity and/or inappropriate activity of the EGFR, exemplary tyrosine kinase inhibitors being erlotinib (Tarceva®), gefitinib (Iressa®), or lapatinib (Tykerb®).

Still other embodiments provide methods of inhibiting a cell proliferative disorder characterized by over-activity and/or inappropriate activity of a receptor comprising administering a pharmaceutically effective amount of a composition comprising a compound capable of mimicking the L858R mutation in the tyrosine kinase domain of the epidermal growth factor receptor (EGFR).

Other embodiments provide method of treating a patient having a disease characterized by over-activity and/or inappropriate activity of an epidermal growth factor receptor (EGFR), comprising the step of administering to a patient in need of such treatment a pharmaceutical composition comprising a compound capable of mimicking the L858R mutation in the tyrosine kinase domain of the epidermal growth factor receptor (EGFR) in an amount in an amount effective to mimic the L858R mutation in the tyrosine kinase domain of the epidermal growth factor receptor (EGFR).

BRIEF DESCRIPTION OF THE DRAWINGS

FIG. 4 illustrates the effect of the EGFR kinase inhibitors on inhibition of tumor cell proliferation by Tarceva®. The inhibitory effect of 20 µM Tarceva® on proliferation of EGFR-expressing NE99 (FIG. 4A) and EGFR-negative T6-17 (FIG. 4B) cell lines has been tested in the absence (closed bars over "Buffer") and presence (closed bars over MMCs) of 0.5 µg/ml concentrations of the designed EGFR kinase inhibitors. The inhibitory effects of each compound in the absence of Tarceva® (open bars) are shown as controls. The compounds enhance the inhibitory effect of Tarceva® on proliferation of the NE99 tumor cells that have high expression levels of EGFR. At the same concentrations, the compounds have no effect on non-EGFR-specific inhibition of T6-17 cell proliferation by Tarceva®.

FIGS. 8A-C illustrates the effects of EEO3 and Tarceva® at 0.25 µM (FIG. 8A) and 1 nM (FIG. 8B) concentrations on anchorage independent growth of NE91 cells. FIG. 8C shows the numbers of soft agar colony formations after three weeks with no treatment, with Tarceva® alone, EEO3 alone or Tarceva® plus EEO3 combination were counted using the AlphaImager 2000 imaging system.

FIG. 12 identifies wild-type amino acid (SEQ ID NO: 2) and corresponding nucleic acid sequences (SEQ ID NO: 1) for the human EGFR kinase domain. Residue number 1 of SEQ ID NOS: 1 and 2 corresponds to residue 695 of FIG. 12, and the remaining residues are numbered consecutively in a corresponding manner (for example, the 858 position in FIG. 12, corresponds to the 164 position of SEQ ID NOS: 1-3). Further, SEQ ID NO: 3 provides an amino acid sequence of human EGFR wherein the leucine residue at position 164 is substituted with arginine (L858R mutation).

DETAILED DESCRIPTION OF ILLUSTRATIVE EMBODIMENTS

Figure 1:
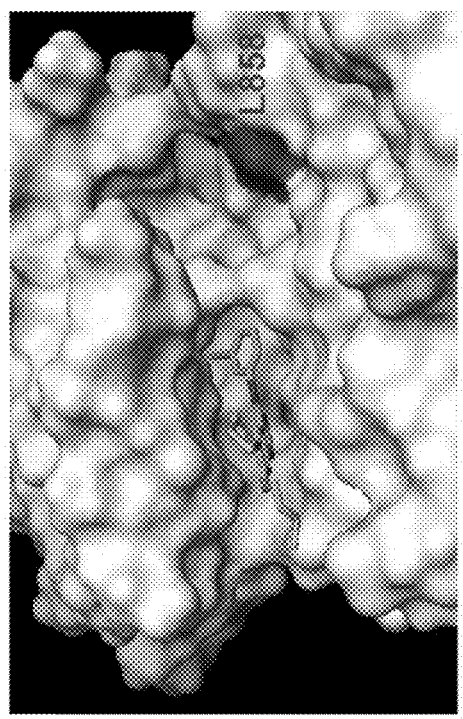
FIG. 1 provides an illustration of one possible representation of the binding of Tarceva® and one MMC (EEO3) in the cavities of the EGFR. The upper panel depicts a possible EGFR-Tarceva® complex, in which Tarceva® binds to the active site of the EGFR kinase close to the L858 residue. The lower panel depicts a possible binding conformation of EEO3 to the wild type (WT) EGFR-Tarceva® complex near the mutation site produces mutation-like effects by stabilizing the EGFR-Tarceva® complex and sensitizing EGFR to Tarceva®-induced inhibition.
Figure 1:
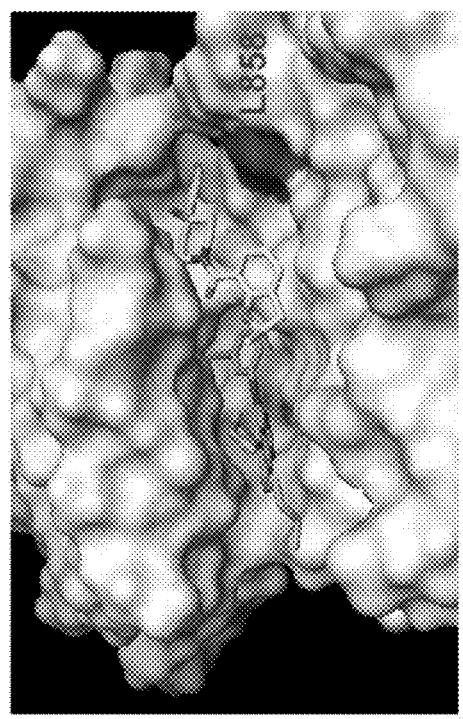
Figure 1:
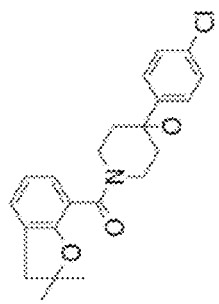

The present inventions are directed to compounds which are useful agents for treating cell proliferative disorders, especially those disorders characterized by over activity and/or inappropriate activity of a EGFR, including EGFR-related cancers, particularly for expanding the efficacy of drugs previously developed for this purpose, and for methods of treatments using the compounds for this purpose.

The present invention may be understood more readily by reference to the following detailed description taken in connection with the accompanying Figures and Examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer both to the compounds and to the resulting pharmaceutical compositions and methods of manufacture and use.

When values are expressed as approximations, by use of the antecedent "about," it will be understood that the particular value forms another embodiment. In general, use of the term "about" indicates approximations that can vary depending on the desired properties sought to be obtained by the disclosed subject matter and is to be interpreted in the specific context in which it is used, based on its function, and the person skilled in the art will be able to interpret it as such. Where present, all ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges includes each and every value within that range.

In certain embodiments, a pharmaceutical composition comprising a compound capable of mimicking the L858R mutation in the tyrosine kinase domain of the epidermal growth factor receptor (EGFR) in an amount in an amount effective to mimic the L858R mutation in the tyrosine kinase domain of the epidermal growth factor receptor (EGFR). Such "mimicking" includes, but is not limited to, causing conformational changes in or on the EGFR or altering the binding properties of the EGFR, consistent with the L858R mutation. For the sake of brevity, the compounds capable of mimicking the L858R mutation in the tyrosine kinase domain of the epidermal growth factor receptor (EGFR) will be referred to as L858R mutation mimicking compounds, or "MMCs."

Other embodiments also provide for the use of these compounds in the preparation of such pharmaceutical compositions.

Non-limiting examples of compounds capable of mimicking this L858R mutation include those compounds having structures of Formulae I-V:

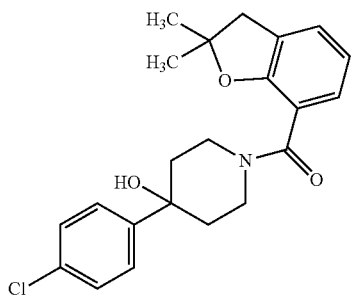

(I)

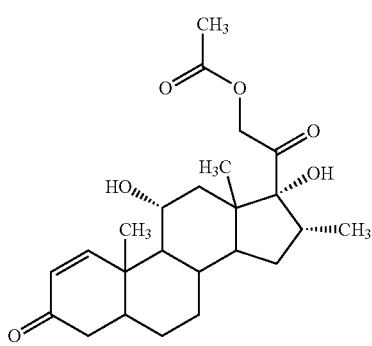

(II)

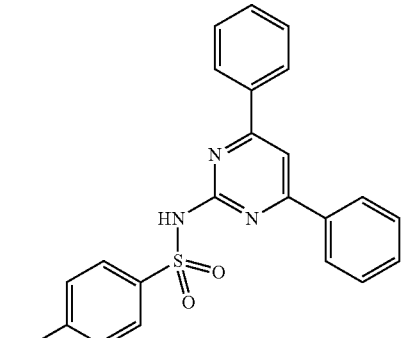

(III)

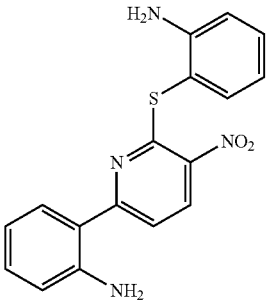

(IV)

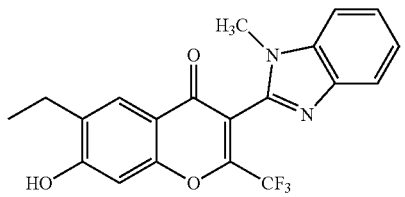

(V)

Throughout this disclosure, these compounds may also be referred to by other designations, reflecting their commercial designation. See following Table.

| Structure | Alternate Designation | Source |
| --- | --- | --- |
| Formula (I) | EEO3 | Maybridge |
| Formula (II) | EEO4 | Maybridge |
| Formular (III) | EKGN1 (NRB00372) | Maybridge |
| Formula (IV) | EEN6A (SEW05581) | Maybridge |
| Formula (V) | EEEO6 (JFD02282) | Maybridge |

Each of these compounds satisfy Lipinski's Rule of 5: i.e., (a) not more than 5 hydrogen bond donors (nitrogen or oxygen atoms with one or more hydrogen atoms); (b) not more than 10 hydrogen bond acceptors (nitrogen or oxygen atoms); (c) A molecular weight not greater than 500 daltons; and (d) an octanol-water partition coefficient log P not greater than 5.

These structures additionally share common attributes as to the extent of their planar or pseudoplanar arrangements of multiple ring systems and the spatial arrangement of the hydrogen bond acceptors and donors, each of which contributes to their ability to fit within the identified EGFR cavity (see below).

Additional embodiments include those wherein the pharmaceutical composition comprises a pharmaceutically acceptable salt or prodrug of a compound having the structure of any one of Formulae I-V, or a homolog or substituted derivative of a compound having a structure of any one of Formulae I-V. The term "homolog or substituted derivative" is intended to connote a structure which provides the spatially positioned array of planar or pseudoplanar of ring systems of any one of Formulae I-V and optionally the spatial arrangement of the hydrogen bond acceptors and donors of a structure of any one of Formulae I-V, together with satisfying Lipinski's Rule of 5, so as least not to compromise, and preferably improve, the binding ability of the compound with the tyrosine kinase domain of the EGFR described in following paragraph Such homologs or substituted derivative may bind with an affinity to the EGFR cavity (described in following paragraph) more or less as tightly as any of the compounds of Formulae I-V, though more tightly is preferred.

Figure 2:
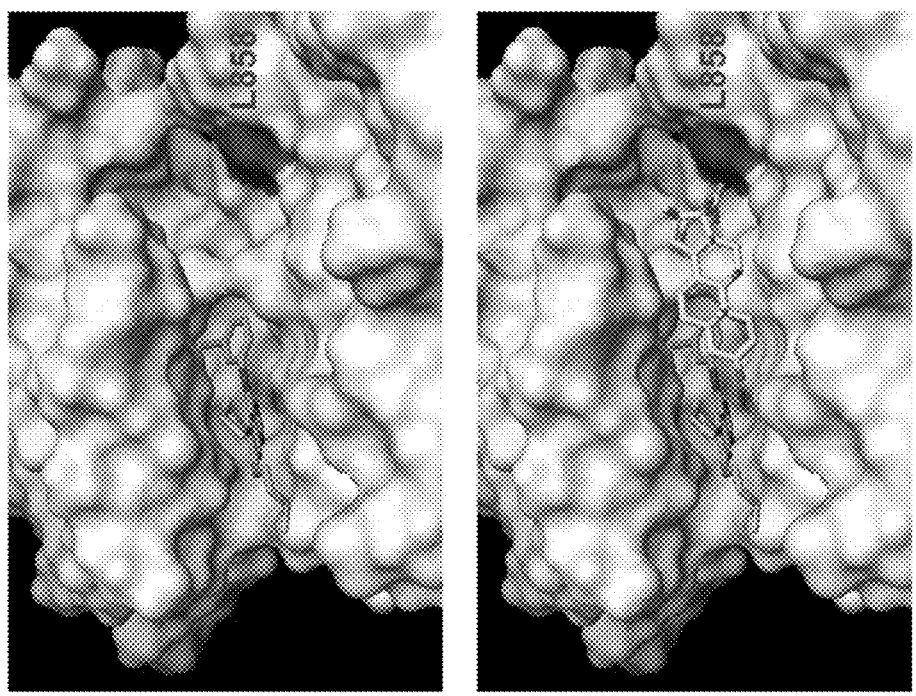
FIG. 2 provides a second illustration of one possible representation of the binding of Tarceva® and one MMC (EEO4) in the cavities of the EGFR.
Figure 2:
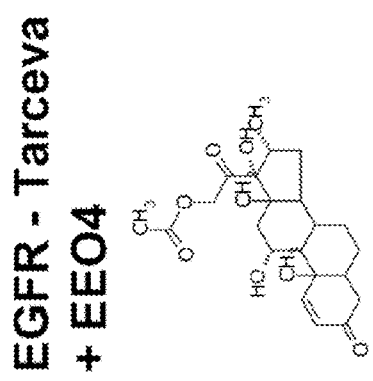

In various embodiments, the MMCs of the present invention, including but not limited to the compounds of Formulae I-V, bind or may be characterized by their ability to bind with an affinity to the cavity on the tyrosine kinase domain of the EGFR, said cavity defined by the residues G719-F723, V726, K745, L747, A755, E758, I759, D761, E762, C797, L799, D800, D837, R841, N842, D855, G857, L858, K875, P877 of human EGFR, shown in FIG. 12 (Note that the corresponding residues in SEQ. ID NOS.: 1-2 are G25-F29, V32, K51, L53, A61, E64, I65, D67, E68, C103, L105, D106, D143, R841, N148, D161, G163, L164, K181, P183). Such an affinity may be relative to the affinity of the specific compounds provided herein or with respect to an absolute dissociation constant (described below). As used herein, the term "target cavity" is that cavity defined by these residues. The present inventors first postulated that the interaction of small molecules within this target cavity might provide the desired effect of mimicking the drug-sensitizing effect of the EGFR kinase domain mutations. Without intending to be bound by any particular theory, it appears that, upon binding, these compounds may cause conformational changes within the tyrosine kinase domain so as to mimic the conformation of this domain when mutated by the replacement of Leu-858 with Arg-858. This concept is illustrated in FIG. 1 and FIG. 2.

This affinity, or ability to bind to the target cavity, can also be used to identify a broader range of chemicals than the structures cited above. The following methodology and the chemicals derived from its use—either as contained in pharmaceutical compositions or for the use in treatment of one or more disorders characterized by over-activity and/or inappropriate activity of an epidermal growth factor receptor (EGFR)—constitute additional embodiments of the present invention.

The mutation mimicking compounds of the present invention can be identified by their binding affinity to the target cavity. At a first level, this can be accomplished through use of commercial software packages which are capable of identifying low-energy binding modes of small molecules, or ligand, within the identified target cavity. One non-limiting example of such software is the widely distributed DOCK software, version 4.0, Ewing, et al., "DOCK 4.0: search strategies for automated molecular docking of flexible molecule databases," J. Comput. Aided Mol. Des., 15: 411-428 (2001). The DOCK software is but one commercial software packages used for this purpose, and it is expected that other such software packages may be useful for this screening purpose. Screening of two commercial compound databases from Maybridge and Asinex with the DOCK software led to the identification of the compounds of Formulae I-V, which when tested (see below) each exhibited the desired binding effects. Having defined the utility of screening against this cavity, and the positive results of compounds identified by this screening, it is expected that the screening of other databases, or individual compounds, using the methods described herein will also yield other compounds of similar or improved activity for the present purpose.

The DOCK screening software, and other similar programs, generally do not provide absolute estimates of binding affinities, rather providing relative rankings. Embodiments of the present invention, then, include those compounds characterized by having relative binding affinities, as estimated by the DOCK software, version 4.0, of at least those exhibited by any of the compounds of Formulae I-V.

Figure 3:
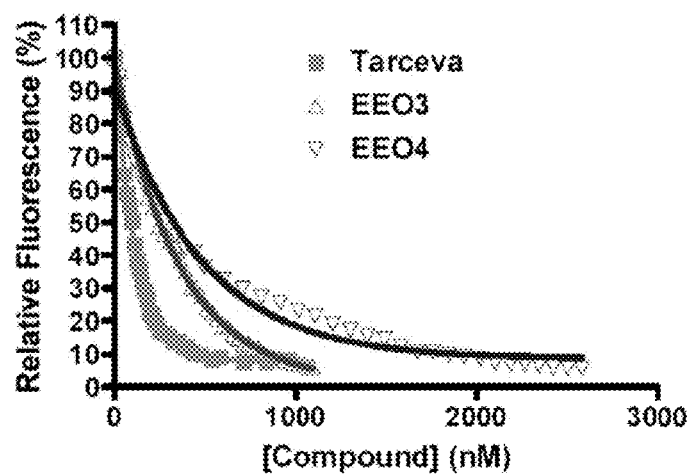
FIG. 3 shows curves of percent fluorescence as a function of MMC concentration for EEO3 and EEO4, and the associated binding constants derived therefrom.

Further embodiments also include those compounds whose experimentally derived binding constants are at least as high as these compounds of Formulae I-V compounds, when measured using either Intrinsic Fluorescence or Isothermal calorimetry methods. FIG. 3 shows exemplary fluorescence and binding (dissociation constant) data for several compounds. Separate embodiments provide that the complexes that form between an MMC and EGFR exhibit dissociation constants, $K_D$ of about 1000 nM or less, are about 500 nM or less, are about 400 nM or less, are about 350 nM or less, are about 300 nM or less, are about 250 nM or less, and are about 100 nM or less, when measured using one or both of the methods described in Example 1.

MMCs also exhibit the characteristic that their binding affinities to non-mutated EGFR are substantially higher than their binding affinities to EGFR having the L858R mutation. That is, while the binding affinity of the compounds tested in non-mutated EGFR defined by the cavity described above (and when Leu is present in the 858 position), when the single mutation is introduced such that Leu-858 is replaced by Arg-858—the binding affinity drops dramatically. FIG. 6B shows that EEO3 does not activate EGFR phosphorylation in the cell line expressing the mutant form of EGFR (compare lanes 1 and 2) as it does in cell lines expressing WT EGFR. Also, unlike its effect in wild type cell lines, EEO3 does not enhance Tarceva®-induced inhibition of EGFR phosphorylation in the mutant cell line (compare lanes 7 and 8)". Similarly, as described herein, EEO3 does not produce its mutation mimicking effects ((1) enhancement of constitutive phosphorylation of EGFR in the absence of EGF and (2) enhancement of Tarceva®-induced inhibition of EGFR phosphorylation in the presence of EGF) in cells expressing mutant EGFR. Accordingly, MMCs may be characterized as having a higher binding constant (lower dissociation constant) for non-mutated vs. L858R mutated EGFR.

Figure 5:
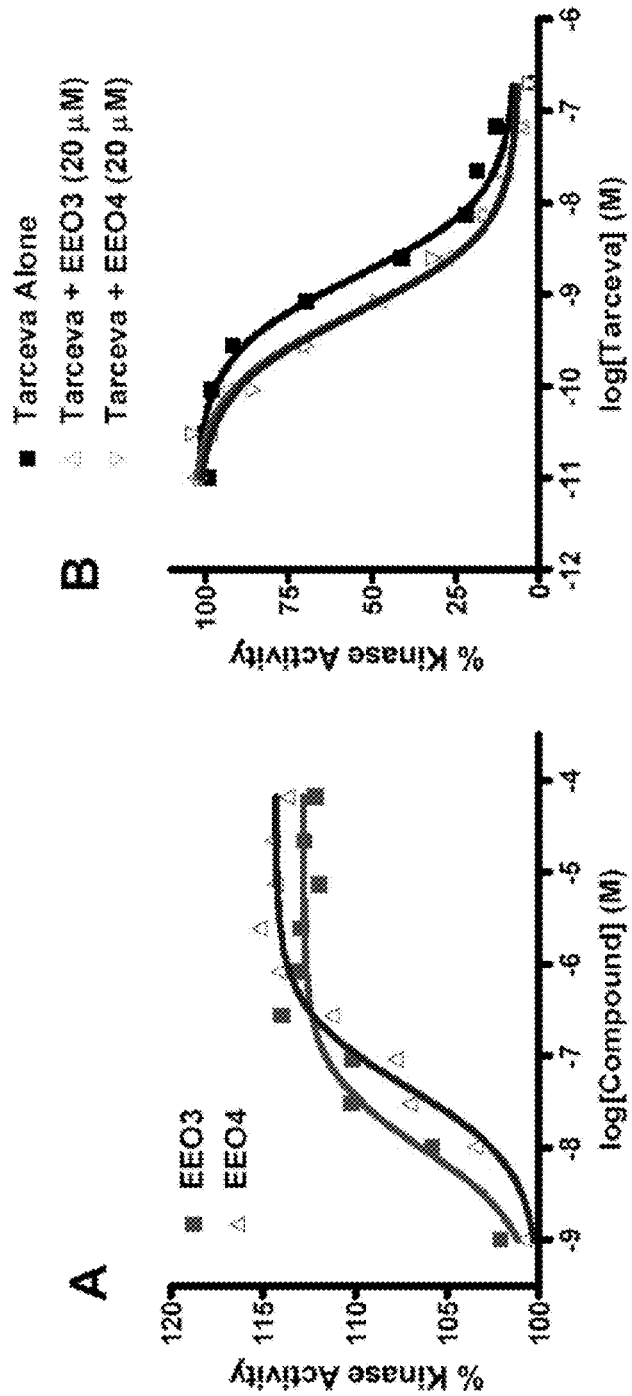
FIG. 5 illustrates the effect of EEO3 and EEO4 on the enzymatic activity of a purified EGFR kinase (FIG. 5A) and on the inhibition of EGFR kinase by Tarceva® (FIG. 5B). The kinase activity was measured using a standard $^{33}P$ radioisotope assay that has been described in previous publications.

The binding affinity of tyrosine kinase inhibitors is enhanced by the presence and binding of the MMCs. For example, FIG. 5B shows that the binding of Tarceva® to EGFR is enhanced by about 2-3-fold in the presence of EEO3 and EEO4. Accordingly, in certain embodiments of the present invention, the compound capable of mimicking the L858R mutation, when present in a pharmaceutical composition of when used to treat a patient or condition, increases the affinity between small molecule tyrosine kinase inhibitors and the tyrosine kinase domain of the epidermal growth factor receptor by at least a factor of 2, or at least a factor of 3, when measured by a standard binding affinity, which may include a $^{33}P$ radioisotope assay.

MMCs can also be characterized by the consequences of their binding to EGFR. Previous studies have shown that mutant EGFRs selectively activate Akt and signal transduction and activator or transcription (STAT) signaling pathways, which promote cell survival, but have no effect on extracellular signal-related kinase signaling which induces proliferation. See Sordella, et al., "Gefitinib-Sensitizing EGFR Mutations in Lung Cancer Activate Anti-Apoptotic Pathways," *Science*, Vol. 305, 20 Aug. 2004, pp. 1163-67, which is incorporated herein by reference in its entirety. These studies show that, when tested with tyrosine-specific antibody, mutated EGFR provides for an enhanced constitutive phosphorylation of total EGFR and/or an enhanced constitutive phosphorylation of Tyr 845 and/or Tyr 1068, but has little or no effect on constitutive phosphorylation of Tyr 992, compared with non-mutated EGFR alone, when tested using the same tyrosine-specific antibody. MMCs bound to non-mutated EGFR elicit the same response as described for the mutated EGFRs. Accordingly, embodiments of the present invention include those wherein, when tested with tyrosine-specific antibody, mutated EGFR provides for an enhanced constitutive phosphorylation of total EGFR and/or an enhanced constitutive phosphorylation of Tyr 845 and/or Tyr 1068, but has little or no effect on constitutive phosphorylation of Tyr 992, compared with non-mutated EGFR alone, when tested using the same tyrosine-specific antibody. The degrees of enhancement or non-enhancement can be quantified by the information provided herein. That is, while the specific data described herein were derived from individual and specific compounds, certain embodiments provide that the relative enhancements seen are quantitatively representative of those available from the greater class of MMCs.

In vitro studies involving the presently identified compounds show that MMCs can be used to enhance Tarceva®-induced inhibition of EGFR phosphorylation in EGFR expressing tumor cells. In vitro studies have also shown that enhancement of Tarceva®-induced inhibition of EGFR phosphorylation in tumor cell lines results in stronger biological activity of Tarceva® against tumor cells. Note that Tarceva® is believed to be representative of other tyrosine kinase inhibitors in its ability to elicit certain of the biological responses described herein, such that data generated using this tyrosine kinase inhibitor may be considered to read more generally to this class of inhibitors.

Figure 4C:
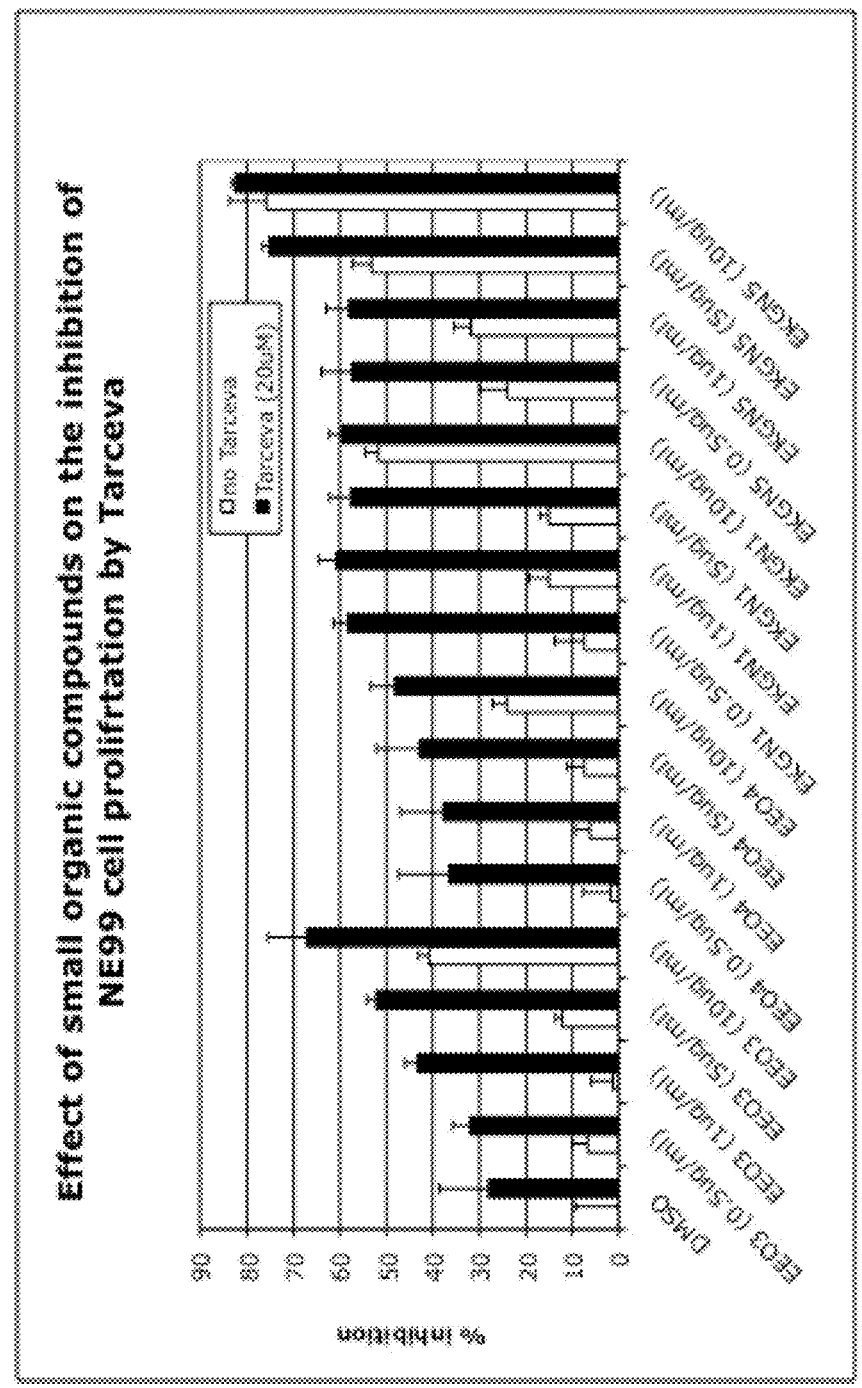
FIG. 4C shows results of a broader range of testing.

FIG. 4 provides data which show that MMCs enhance the inhibitory effect of Tarceva® on the proliferation of EGFR-expressing NE99 tumor that have high expression levels of EGFR, while at the same concentrations, the compounds have not effect on non-EGFR-specific inhibition of T6-17 cell proliferation by Tarceva®. More generally, then, in certain embodiments MMC compounds are characterized by their ability to enhance the inhibitory effect of Tarceva® on the proliferation of NE99 tumor cells, by amounts at least as high as shown in FIG. 4, when applied with Tarceva®, relative to Tarceva® alone. A standard MIT assay protocol, previously published and generally understood by those skilled in the art, was used in this experiment.

MMCs also show an activating effect on the activity of a purified EGFR kinase domain (FIG. 5A) and enhance Tarceva®-induced inhibition of EGFR activity by about 3-fold (FIG. 5B), supporting a view that the MMCs stabilize the active form of EGFR kinase thereby making it more susceptible to tyrosine kinase inhibitors. (In FIG. 5A, "100% kinase activity" refers to kinase activity in the absence of inhibitors. In the presence of increased concentrations of inhibitors, the kinase activity decreases and KD values can be estimated from the obtained S-shaped curves).

Figure 6A:
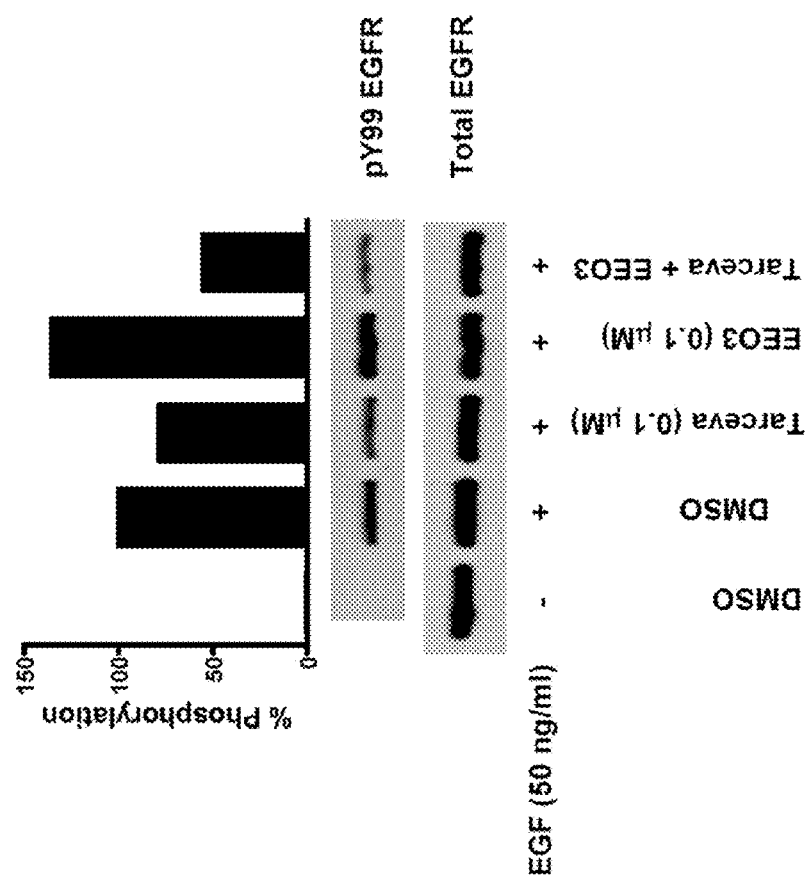
FIG. 6A is a Western blot analysis illustrating the effect of EEO3 on the inhibition of EGFR phosphorylation by Tarceva® in NE91 cells. EGF-induced phosphorylation of EGFR was tested in the presence and absence of Tarceva® alone and Tarceva®+EEO3 combination. Total EGFR levels were measured as a control.
Figure 6B:
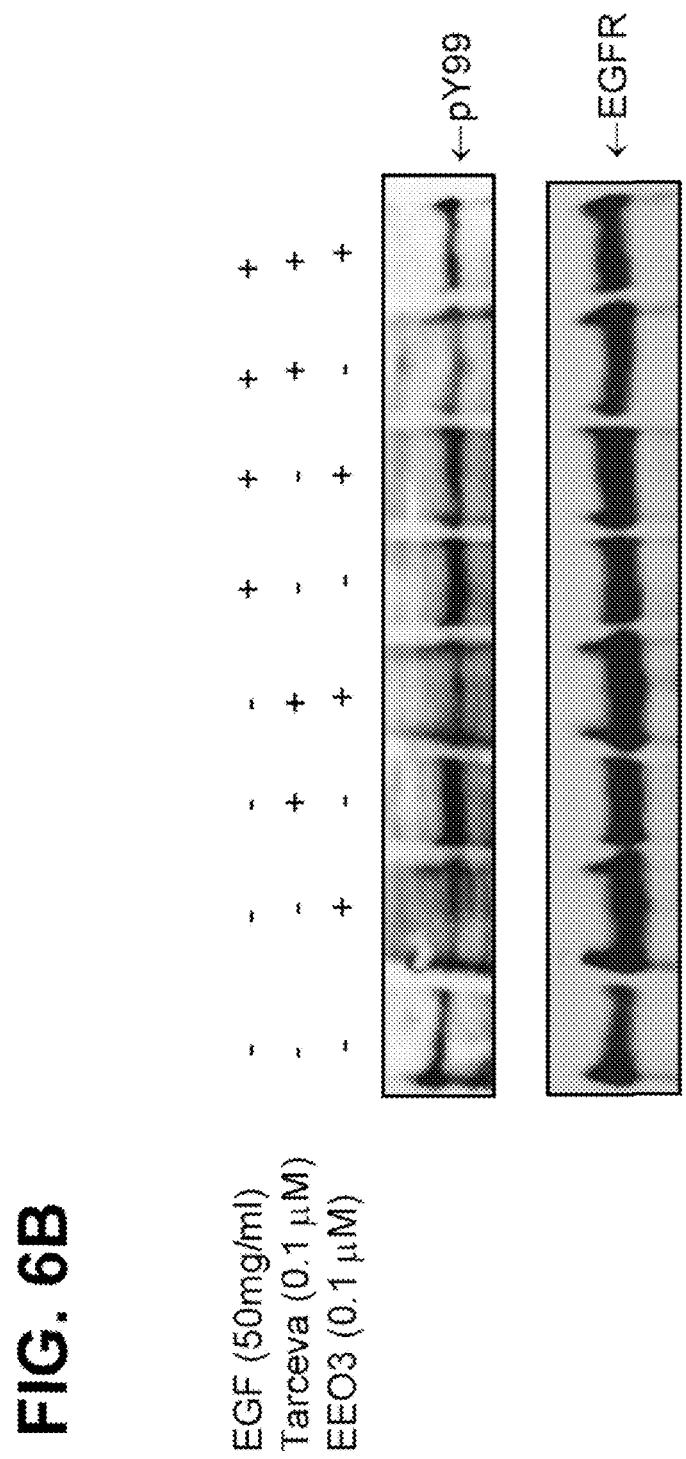
FIG. 6B shows the effect of Tarceva® and EEO3 on the phosphorylation in mouse fibroblasts expressing L858R EGFR.

In FIGS. 6A-B, the data show that MMCs (in this case EEO3) show a distinguishing and characteristic ability to mimic two well-documented effects produced by the drug-sensitizing tyrosine kinase mutations of EGFR: (1) enhancement of receptor phosphorylation due to stabilization of the activated conformation of the EGFR kinase domain (track 3), and (2) enhancement of Tarceva®-induced inhibition of EGFR phosphorylation because of the increased affinity of Tarceva® for the activated form of the EGFR kinase (track 4). No changes in total EGFR levels were detected in the presence of EEO3 suggesting that the observed mutation-mimicking effects were mediated by direct binding of EEO3 to the kinase domain of EGFR and not by non-specific effects on EGFR expression. Generalizing these results, in certain embodiments, MMCs can be characterized by their ability to increase the phosphorylation of pY99 EGFR by at least 25% (relative to a blank standard) and to enhance the Tarceva®-induced inhibition of the same phosphorylation by at least about 20%, when tested according to the conditions of FIGS. 6A-B.

As described above, these MMCs can also reproduce some other important features of the mutant receptors including enhanced constitutive phosphorylation of total EGFR, enhanced constitutive phosphorylation of specific Tyr residues, and enhanced susceptibility of the downstream AKT and ERK signaling to inhibition by Tarceva® (FIG. 7). As described above, the L858R mutation is known to result in enhanced constitutive phosphorylation of total EGFR as well as Tyr 845 and Tyr 1068, but to have no effect on constitutive phosphorylation of Tyr 992. See Choi et al., "EGF-independent activation of cell-surface EGF receptors harboring mutations found in getifinib-sensitive lung cancer," *Oncogene*, 26, 1567-1576 (2007), which is incorporated by reference herein in its entirety. These specific mutation-like effects are also observed upon addition of the MMCs. These MMCs enhance constitutive phosphorylation of total EGFR (FIG. 7, upper panel), of Tyr 845 (FIG. 7, panel 2 from top) and of Tyr 1068 (FIG. 7, panel 3 from top), but have no effect on constitutive phosphorylation of Tyr 992 (FIG. 7, panel 4 from top). Also similar to the effects produced by the mutation, the compounds enhance Tarceva®-induced inhibition of phosphorylation of total EGFR (FIG. 7, upper panel), of Tyr 845 (FIG. 7, panel 2 from top), of Tyr 1068 (FIG. 7, panel 3 from top) and of the downstream signaling molecules including AKT (FIG. 7, panel 5 from top) and ERK (FIG. 7, panel 6 from top).

Figure 8C:
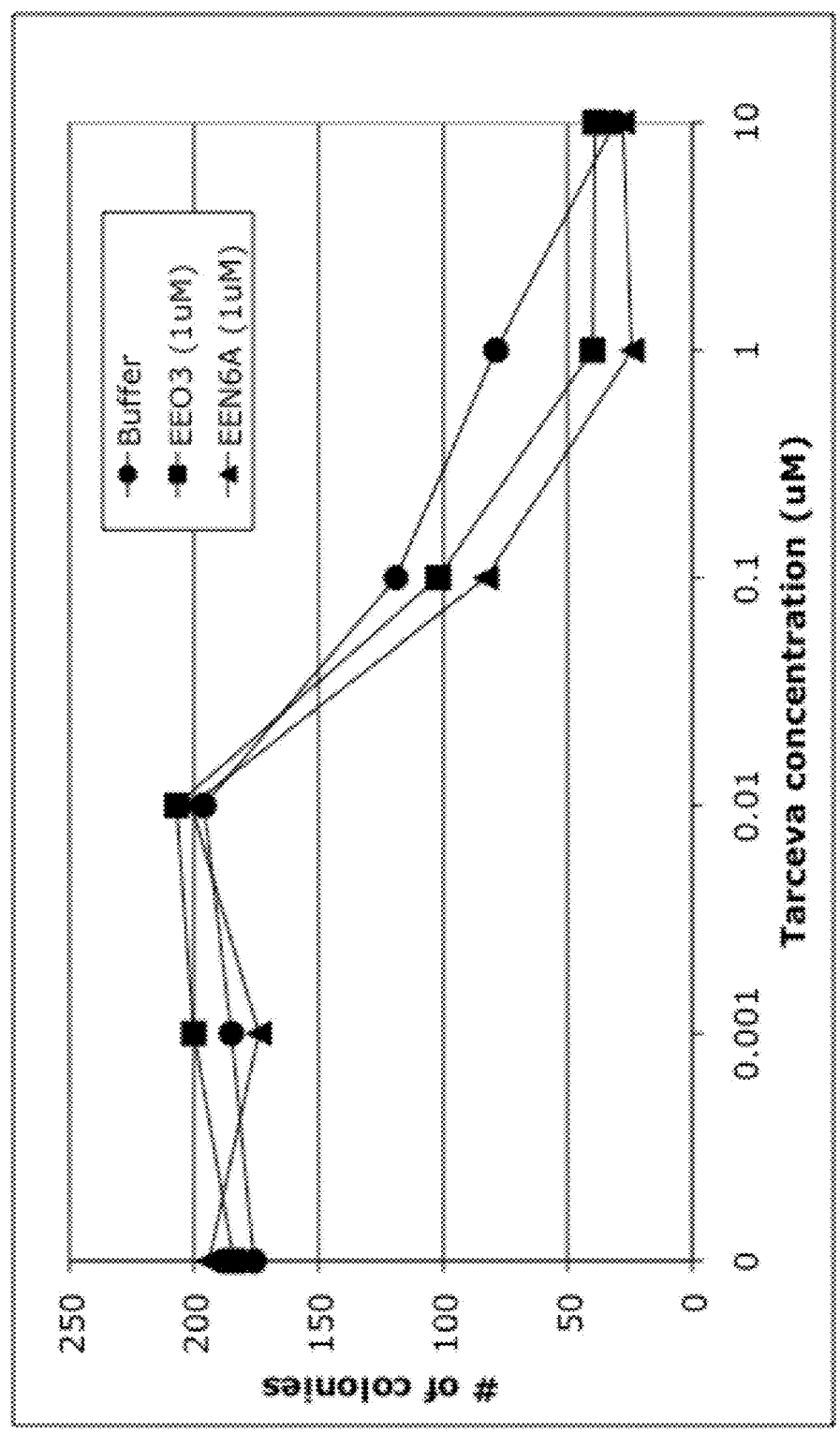

FIGS. 8A-C show that the described two mutation-mimicking effects of EEO3, as a representative MMC, on EGFR phosphorylation result in corresponding effects in vitro on the anchorage independent growth of EGFR-overexpressing NE91 cells (See Example 5 for test conditions). Indeed, EEO3 alone stimulated cell growth (FIG. 8A). Despite the activating effect when used as a single agent, EEO3 enhanced the inhibitory effect on cell growth when used in combination with Tarceva® (FIG. 8A). The observed enhancement of the inhibitory effect of Tarceva® on colony formation in EGFR-overexpressing cells was even more dramatic when EEO3 was used in combination with a low concentration of Tarceva® that does not have any inhibitory effect by itself (FIG. 8B). Since the clinical effect of Tarceva® is known to be limited by its toxicity at high therapeutic doses, the observed sensitization of EGFR expressing cells to Tarceva® in the presence of EEO3 may offer significant clinical advantages. The new data support the hypothesis that binding of EEO3 to the tyrosine kinase domain of EGFR produces effects similar to the drug-sensitizing kinase domain mutations resulting in (1) stabilization of the activated conformation of the kinase domain with increased Tarceva® binding affinity and (2) increased susceptibility of the EGFR-overexpressing cells to the tyrosine kinase inhibitors.

EGFR tyrosine kinase inhibitors have been shown to induce apoptotic effect in cells with mutant EGFR, but not in cells with wild type EGFR. One of the many significant features or consequences of the ability of the inventive MMCs to mimic the L858R mutation is the associated ability to enhance the effectiveness of previously identified drugs designed to inhibit a cell proliferative disorder characterized by over-activity and/or inappropriate activity of the EGFR. That is, administration of the designed MMCs to patients with wild-type EGFR is expected to make them more susceptible to treatment with the clinically used tyrosine kinase inhibitors. Accordingly, various embodiments of the present invention include pharmaceutical compositions comprising both one or more MMC and a tyrosine kinase inhibitor, preferably a small molecule tyrosine kinase inhibitor.

Exemplary tyrosine kinase inhibitors include erlotinib (Tarceva®), gefitinib (Iressa®), and lapatinib (Tykerb®), but may also include molecules more broadly described in U.S. Pat. Nos. 5,747,498; 6,900,221; 7,087,613; RE41065 (corresponding to Erlotinib); U.S. Pat. Nos. 5,457,105; 5,616,582; 5,770,599 (corresponding to Gefitinib); U.S. Pat. Nos. 6,391,874; 6,713,485; 6,727,256; 6,828,320; and 7,157,466 (corresponding to Lapatinib), each of which is incorporated by reference herein in its entirety. These tyrosine kinase inhibitors are believed to bind to the adenosine triphosphate (ATP) pocket within the catalytic domain of the EGFR. See, Sordella, et al., "Gefitinib-Sensitizing EGFR Mutations in Lung Cancer Activate Anti-Apoptotic Pathways," *Science*, Vol. 305, 20 Aug. 2004, pp. 1163-67, which is incorporated herein by reference in its entirety.

Figure 9:
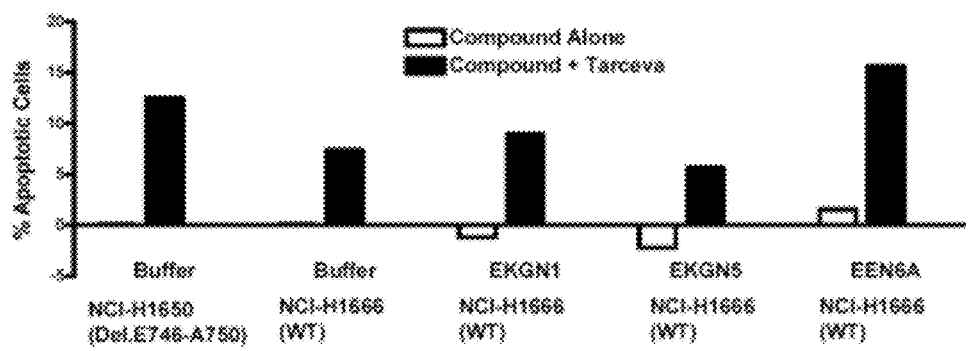
FIG. 9 illustrates the effect of MMCs on the apoptotic activity of Tarceva® in wild type (non-mutated) and mutant EGFR expressing cell lines. The cells were incubated in RPMI medium with 0.5% FBS in the presence of 1 µM Tarceva®, 1 µM compound or Tarceva® +compound combination for 48 hrs, then stained with annexin V and analyzed by FACS.
Figure 9:
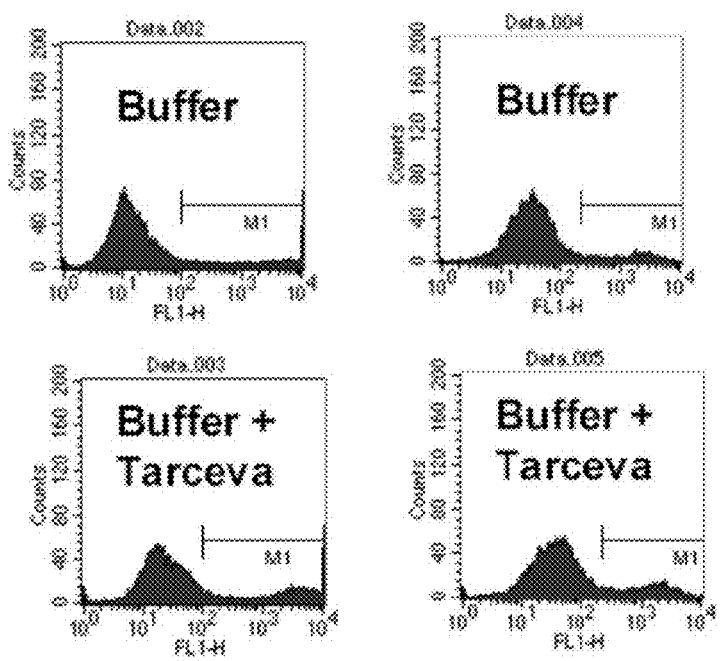
Figure 9:
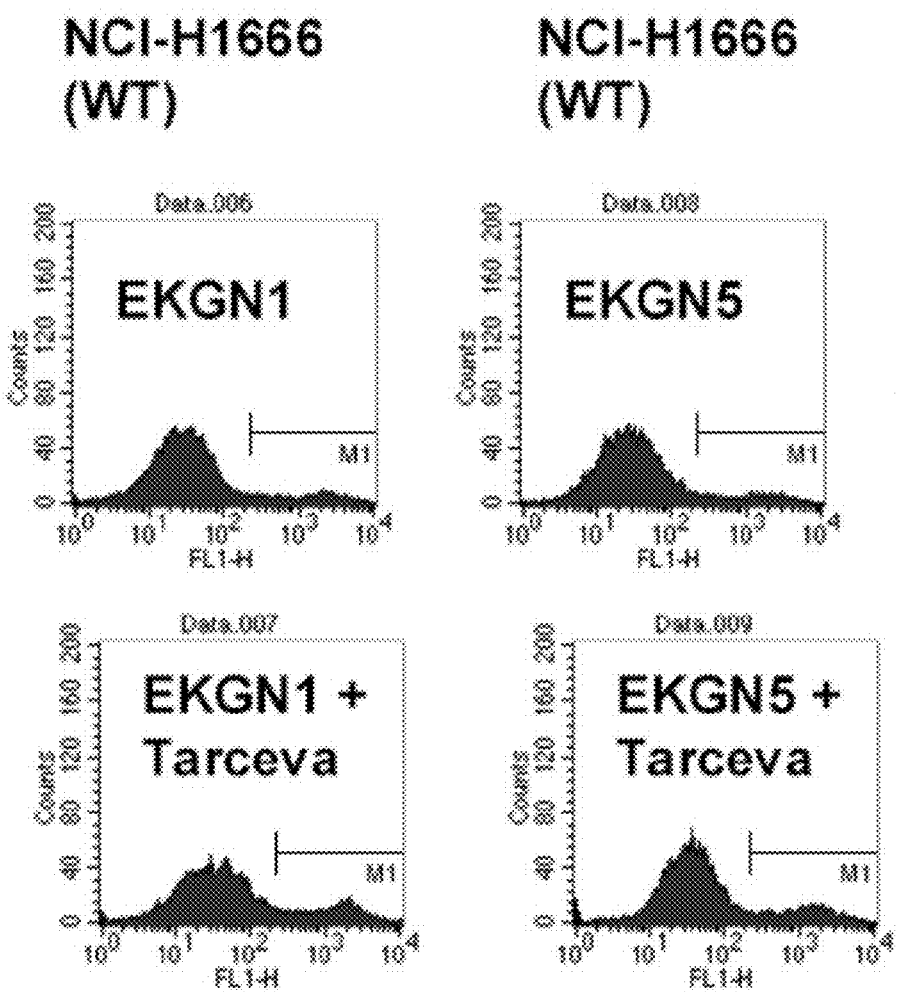
Figure 9:
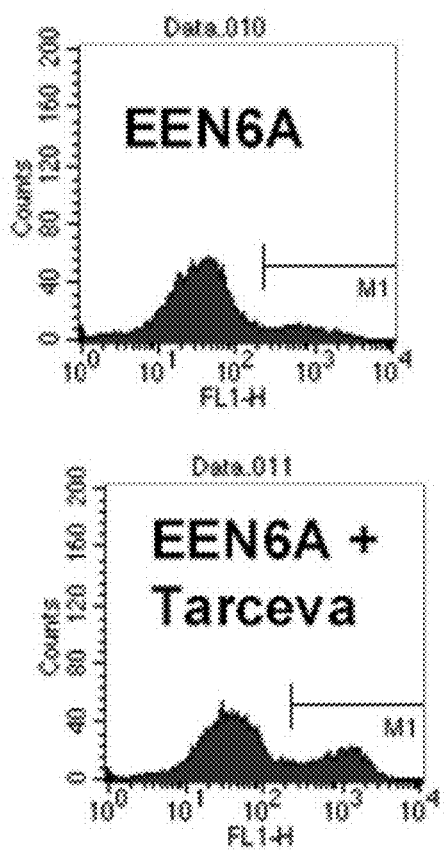

The effectiveness of representative MMCs in this capacity is shown in FIG. 9, which shows the results of testing of several MMCs on the ability of Tarceva® to induce apoptosis in wild-type (non-mutated) EGFR expressing NCI-H1666 cells. The results obtained in the presence of the compounds were compared with the effects produced by Tarceva® in mutant EGFR expressing NCI-H1650 cells. As expected, Tarceva® had a stronger apoptotic activity in mutant cells when used alone. However, in the presence of one of the MMCs, EEN6A, the apoptotic activity of Tarceva® in wild-type (non-mutated) EGFR expressing cell line increased to the level observed with Tarceva® alone in the mutant cell line. The obtained result confirmed that EEN6A enhances the apoptotic activity of Tarceva® similar to the effect produced by an activating mutation in the EGFR kinase domain.

Figure 10B:
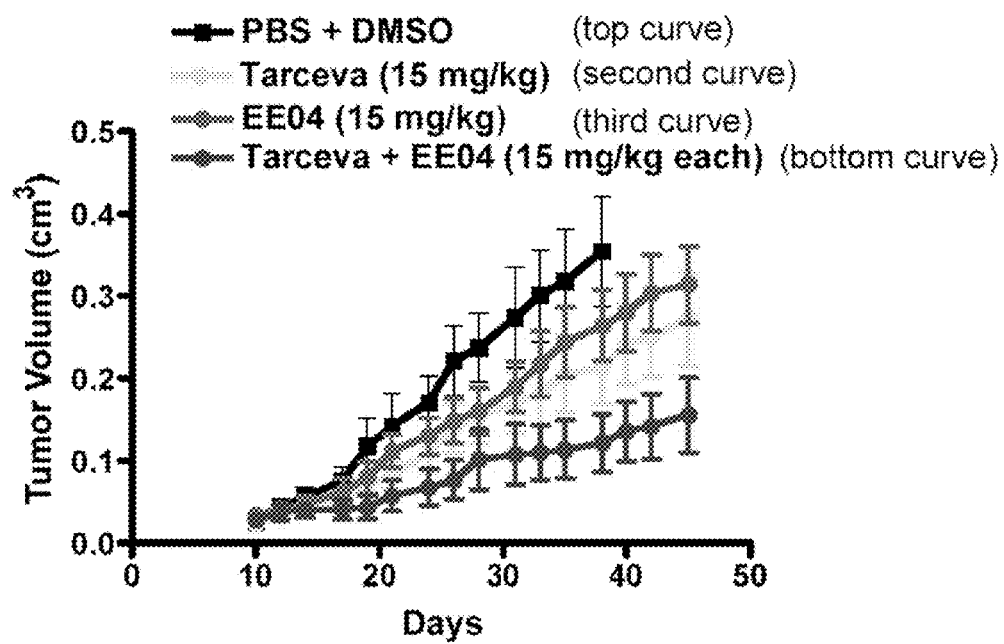
FIG. 10 graphically represents the results of in vivo testing of EEO3 (A) and EEO4 (B) in mice with AsPC1 tumors.

Further, the inventive MMCs are shown to significantly enhance the anti-tumor effect of Tarceva® in mice. The results of in vivo tests in mice with AsPC1 pancreatic tumors in shown in FIG. 10. Tarceva® by itself had only a modest effect on tumor growth at 15 mg/kg when used as a single agent (second curve from the top in FIG. 10). Likewise, EEO3 on its own had a weak antitumor effect similar to Tarceva® alone (third curve from the top in FIG. 10). However, combining Tarceva® with 15 mg/kg of EEO3 resulted in significant synergistic antitumor effect (lowest curve in FIG. 10).

Again, the compounds of Formulae I-V were identified as having at least one of the defining characteristics of MMCs through screening experiments—i.e., that the fit within the target cavity resulted in a low energy state (high binding affinity) of the resulting complex. The apparent absence of a generalized chemical structure should probably be seen as reflecting the contents of the chemical libraries screened more than the preclusion of related chemistries. Accordingly, in various embodiments, the compounds of the present invention include those analogs, homologs, salts, and derivatives of the compounds of Formulae I-V. Similarly, given the proximity of the ATP pocket with the cavity defined for the MMCs, additional embodiments of the present invention comprise those compounds, and pharmaceutical compositions comprising these compounds, which contain the functional features responsible for the binding of each of the tyrosine kinase inhibitors and the MMCs as described above, wherein these individual functional features are linked together within the compounds so as to allow the respective functional features of the tyrosine kinase inhibitors and the MMCs to bind to their respective binding sites. This concept is more fully developed in U.S. Patent Application Ser. Nos. 61/453,682 and 61,486,453, filed Mar. 17, 2011 and May 16, 2011, respectively, and entitled "Methods and Use of Bifunctional Enzyme-Building Clamp-Shaped Molecules," each of which is incorporated by reference herein in its entirety for all purposes.

Thus far, this disclosure has provided pharmaceutical compositions comprising compounds which, either by themselves or with tyrosine kinase inhibitors, are useful for the treatment of a cell proliferative disorder characterized by over-activity and/or inappropriate activity of the EGFR. Additional embodiments provide for the treatments themselves which complement the compositions themselves; that is, for methods of inhibiting a cell proliferative disorder characterized by over-activity and/or inappropriate activity of a receptor and methods of treating a patient having a disease characterized by over-activity and/or inappropriate activity of an epidermal growth factor receptor (EGFR). Such methods comprise administering a pharmaceutically effective amount of a composition comprising a compound capable of mimicking the L858R mutation in the tyrosine kinase domain of the epidermal growth factor receptor (EGFR). That is, these methods may comprise administering compositions containing the compounds having the characteristics described above.

In certain of these embodiments, the cell proliferative disorder is an EGFR-related disorder, including psoriasis, arthritis, bronchitis, and cancer. In certain embodiments, the cell proliferative disorder is an EGFR-related cancer. In other embodiments, the cell proliferative disorder affects an anus, breast, colon, prostate, lung (including non-small cell lung cancer), pancreas, ovary, or stomach. Methods of treatment may be applied generally wherein the patient is a mammal and specifically to when the patient is a human.

The methods comprising the administration of the pharmaceutical compositions comprising MMCs, either with or without tyrosine kinase inhibitors, may be part of a combination therapy. This combination therapy may include administering a pharmaceutically effective amount of an anti-cancer agent or performing a non-drug therapy or both to the patient. When applied, the anti-cancer agent may be administered within the same composition or at the same time as, or before or after the composition comprising the compound capable of mimicking the L858R mutation. When applied, the non-drug therapy may include surgery, hypertensive chemotherapy, gene therapy, thermotherapy, cryotherapy, photodynamic therapy, laser cauterization and/or radiotherapy.

Pharmaceutical Compositions

As described above, the compounds described in the preceding section are useful for inhibiting a cell proliferative disorder characterized by over-activity and/or inappropriate activity of an EGFR. Pharmaceutical compositions derived from each of the various embodied compounds described above are considered within the scope of this invention. Additionally, the use of any of the previously described compounds are considered to provide separate embodiments for the preparation of a medicament for the inhibition of a cell proliferative disorders characterized by over-activity and/or inappropriate activity of an epidermal growth factor receptor (EGFR). In this regard, commercial packages comprising any of the pharmaceutical composition within the scope of this invention and a written matter associated therewith, the written matter stating that the pharmaceutical composition can or should be used for the prophylaxis and/or treatment of a disease caused by overexpression or aberrant activation of EGFR are also considered within the scope of this invention.

The invention contemplates those compositions wherein the compound exists as a pharmaceutically acceptable salts, as well as prodrugs and metabolites of these compounds.

The term "pharmaceutically acceptable salt" means those salts of compounds of the invention that are safe and effective for use in a subject and that possess the desired biological activity. Pharmaceutically acceptable salts include salts of acidic or basic groups present in compounds of the invention. Various pharmaceutically acceptable salts, ether derivatives, ester derivatives, acid derivatives, and aqueous solubility altering derivatives of the active compound also are encompassed by the present invention. The present invention further includes all individual enantiomers, diastereomers, racemates, and other isomers of the compound. The invention also includes all polymorphs and solvates, such as hydrates and those formed with organic solvents, of this compound. Such isomers, polymorphs, and solvates may be prepared by methods known in the art, such as by regiospecific and/or enantioselective synthesis and resolution, based on the disclosure provided herein.

As the compounds of the invention may contain charged side chains or termini, they may be included in any of the above-described formulations as the free acids or bases or as pharmaceutically acceptable salts. Pharmaceutically acceptable salts are those salts which substantially retain the physiological activity of the free bases and which are prepared by reaction with inorganic acids. Pharmaceutical salts tend to be more soluble in aqueous and other protic solvents than are the corresponding free base forms. For a review on pharmaceutically acceptable salts see Berge et al., 66 J. Pharm. Sci 1-19 (1977), incorporated herein by reference.

Prodrugs and active metabolites of compounds disclosed herein are also within the scope of the invention. A prodrug is a pharmacologically inactive compound that is converted into a pharmacologically active agent by a metabolic transformation or any other chemical or biological process (e.g., hydrolysis). For example, in vivo, a prodrug can be acted on by naturally occurring enzyme(s) resulting in liberation of the pharmacologically active agent. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in "Design of Prodrugs," ed. H. Bundgaard, Elsevier, 1985, incorporated herein by reference.

An active metabolite is a compound that results from metabolism of another compound after administration of the latter to a subject. Metabolites can be identified by techniques well-known in the art.

Suitable dosage forms include but are not limited to oral, rectal, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterille administration, and other dosage forms for systemic delivery of active ingredients. In a preferred embodiment, the dosage form is suitable for oral administration.

To prepare such pharmaceutical dosage forms, one or more of the aforementioned compounds or a pharmaceutically acceptable salt thereof, are intimately admixed with a pharmaceutical carrier according to conventional pharmaceutical compounding techniques. The carrier may take a wide variety of forms depending on the form of preparation desired for administration.

The compounds of the invention, may be administered to a subject per se or in the form of a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active peptides or peptide analogues into preparations which can be used pharmaceutically. Proper formulation is dependent upon the route of administration chosen.

For parenteral formulations, the carrier will usually comprise sterile water, though other ingredients, for example, ingredients that aid solubility or for preservation, may be included. Injectable solutions may also be prepared in which case appropriate stabilizing agents may be employed.

Parenteral administration may comprise any suitable form of systemic delivery or delivery directly to the central nervous system. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

In preparing the compositions in oral dosage form, any of the usual pharmaceutical media may be employed. Thus, the compounds can be readily formulated by combining the compounds, salts, or analogues with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. In some embodiments, the compounds which satisfy Lipinski's Rule of 5 are used in oral formulations.

In some applications, it may be advantageous to utilize the active agent in a "vectorized" form, such as by encapsulation of the active agent in a liposome, micelle, or other encapsulant medium, or by fixation of the active agent, e.g., by covalent bonding, chelation, assembly, or associative coordination, on a suitable biomolecule, such as those selected from proteins, lipoproteins, glycoproteins, and polysaccharides.

For oral solid formulations such as, for example, powders, capsules and tablets, suitable excipients include fillers such as sugars, such as lactose, sucrose, mannitol and sorbitol: cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For solid oral preparations such as, for example, powders, capsules, caplets, and tablets, suitable carriers and additives include starches, sugars, diluents, granulating agents, lubricants, binders, disintegrating agents and the like. Due to their ease in administration, tablets and capsules represent the most advantageous oral dosage unit form. If desired, tablets may be sugar coated or enteric coated by standard techniques.

Treatment methods of the present invention using formulations suitable for oral administration may be presented as discrete units such as capsules, cachets, tablets, or lozenges, each containing a predetermined amount of the active ingredient as a powder or granules. Optionally, a suspension in an aqueous liquor or a non-aqueous liquid may be employed, such as a syrup, an elixir, an emulsion, or a draught.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

For buccal administration, the compounds may take the form of tablets, lozenges, etc. formulated in conventional manner.

For topical administration the compounds of the invention may be formulated as solutions, gels, ointments, creams, suspensions, etc. as are well-known in the art.

Formulations suitable for parenteral administration usually comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Systemic formulations include those designed for administration by injection, e.g. subcutaneous, intravenous, intramuscular, intrathecal or intraperitoneal injection, as well as those designed for transdermal, transmucosal, oral or pulmonary administration.

Nasal and other mucosal spray formulations (e.g., inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

For administration by inhalation, the compounds for use according to the present invention are conveniently delivered in the form of an aerosol spray from pressurized packs or a nebulizer, with the use of a propellant acceptable as suitable by the pharmaceutical industry. Suitable propellants include, but are not limited to dichlorodifluoromethane, trichlorofluoromethane, dichlorotetrafluoroethane,1,1,1,2-tetrafluoroethane, P-227ea, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

For injection, the compounds of the invention may be formulated in aqueous solutions, preferably in physiologically compatible buffers such as Hank's solution, Ringer's solution, or physiological saline buffer. The solution may contain formulatory agents such as suspending, stabilizing and/or dispersing agents.

Alternatively, the compounds may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

The compounds may also be formulated in rectal or vaginal compositions such as suppositories or retention enemas, e.g., containing conventional suppository bases such as cocoa butter or other glycerides, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippingcott Williams and Wilkins: Philadelphia, Pa., 2000.

The formulation of the present invention can have immediate release, sustained release, delayed-onset release or any other release profile known to one skilled in the art.

The subject receiving the pharmaceutical composition is preferably an animal, more preferably a mammal, and most preferably a human.

The specific dose of a compound administered according to this invention to obtain therapeutic and/or prophylactic effects will, of course, be determined by the particular circumstances surrounding the case, including, for example, the compound administered, the route of administration, and the condition being treated. The compounds are effective over a wide dosage range and, for example, dosages will normally fall within the range of from about 0.0025% to about 5%, more usually in the range of from about 0.005% to about 2%, more usually in the range of from about 0.05% to about 1%, and more usually in the range of form about 0.1% to about 0.5% by weight. These dosage ranges are intended to be indicative and are not intended to limit the scope of the invention in any way.

The amount of the active agent to be administered can typically range from between about 0.01 to about 25 mg/kg/ day, preferably from between about 0.1 to about 10 mg/kg/day and most preferably from between about 0.2 to about 5 mg/kg/day. It will be understood that the pharmaceutical formulations of the present invention need not necessarily contain the entire amount of the agent that is effective in treating the disorder, as such effective amounts can be reached by administration of a plurality of doses of such pharmaceutical formulations.

In a preferred embodiment of the present invention, the compounds are formulated in capsules or tablets, preferably containing 25 to 200 mg of the compounds of the invention, and are preferably administered to a patient at a total daily dose of about 0.5 mg to about 2 g, preferably about 7.5 mg to about 750 mg, more preferably about 15 mg to 750 mg, and most preferably from about 50 to about 200 mg. As but one frame of reference, dose regimens of Tarceva® and Iressa® are listed in the Orange Book as in the range of 25 mg to 250 mg.

A pharmaceutical composition for parenteral administration contains from about 0.01% to about 100% by weight of the active agents of the present invention, based upon 100% weight of total pharmaceutical composition.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver peptides and peptide analogues of the invention. Certain organic solvents such as dimethylsulfoxide also may be employed, although usually at the cost of greater toxicity. Additionally, the compounds may be delivered using a sustained-release system, such as semi-permeable matrices of solid polymers containing the therapeutic agent. Several sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day. Some preferred dosages range from 1 nM to 500 mM. Some preferred dosages range from 1 mM to 500 mM. Some preferred dosages range from 1 mg to 500 mg. Some preferred dosages range from 1000 mg to 3000 mg. Some preferred dosages range from 1500 mg to 5000 mg.

In cases of local administration or selective uptake, the effective local concentration of the compounds may not be related to plasma concentration. One having skill in the art will be able to optimize therapeutically effective local dosages without undue experimentation.

Inhibiting Cell Proliferative Disorders

Additionally, various embodiments provide methods of inhibiting a cell proliferative disorder, or treating a patient having a disease, characterized by over-activity and/or inappropriate activity of an EGFR comprising administering to a patient in need of such treatment a pharmaceutically effective amount of any of the compounds described previously. Specific embodiments provide for methods of inhibiting a cell proliferative disorder or treating a patient by inhibiting a cell proliferative disorder within a patient wherein the cell proliferative disorder is cancer, especially for those cancers related to the over-activity and/or inappropriate activity of an EGFR, for example anal, breast, colon, prostate, lung, pancreas, ovary, or stomach cancer. More specific embodiment include those wherein the patient is a mammal, and even more specific embodiments include those wherein the patient is a human.

In treating a patient, the compounds of the present invention may be administered in combinations with a pharmaceutically effective amount of an anti-cancer agent or performing a non-drug therapy or both to the patient. Exemplary anti-cancer drugs include Erlotinib, Gefitinib, Lapatinib, or any compound having a structure in U.S. Pat. Nos. 5,747,498; 6,900,221; 7,087,613; RE41065 (corresponding to Erlotinib); U.S. Pat. Nos. 5,457,105; 5,616,582; 5,770,599 (corresponding to Gefitinib); U.S. Pat. Nos. 6,391,874; 6,713,485; 6,727,256; 6,828,320; and 7,157,466 (corresponding to Lapatinib). When administered in combination with such an anti-cancer drug, the ratio of the anti-cancer drug to a compound of the present invention may be in the range of about 1:100 to about 100:1. Independent embodiments provide that this range may be about 1:10 to about 10:1, about 1:5 to about 5:1, about 1:2 to about 2:1, or about 1:1.

These anti-cancer agents may be administered at the same time, or at different times as part of an overall regimen of treatment. Non-drug therapy may include surgery, hypertensive chemotherapy, gene therapy, thermotherapy, cryotherapy, photodynamic therapy, laser cauterization and/or radiotherapy. The compounds of the present invention may be administered before or after (to prevent recurrence) any of these non-drug therapies. In one preferred embodiment, a patient having had a tumor associated with the cell proliferative disorder, wherein the tumor has been surgically removed, may be treated with a compound of the present invention to prevent recurrence or to inhibit metastasis of the disorder.

As used herein, the term therapeutic agent" is intended to mean a compound that, when present in a therapeutically effective amount, produces a desired therapeutic effect on a patient; for example, utilized to treat, combat, ameliorate, prevent or improve an unwanted condition or disease of a patient. Such inhibition may occur for example, and without limitation, via a direct interaction, and/or through a competitive interaction, or via an allosteric interaction with a corresponding receptor.

A "therapeutically effective amount" or "effective amount" of a composition is a predetermined amount calculated to achieve the desired effect. The activity contemplated by the present methods includes both medical therapeutic and/or prophylactic treatment, as appropriate. As used herein, "therapeutically effective amount" refers to the amount of active compound or pharmaceutical agent that elicits a biological or medicinal response in a tissue, system, animal, individual or human that is being sought by a researcher, veterinarian, medical doctor or other clinician, which includes one or more of the following as specified in the particular methodology: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology' or symptomatology of the disease, condition or disorder (i.e., reducing the severity of the pathology and/or symptomatology).

The term "prevent" as used herein to describe the action of inhibiting cell proliferation or the growth of tumors, or ameliorating the symptoms, prolonging the survival of, or otherwise mitigating the undesirable effects of the disease for which the patient is being treated.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response with or without excessive levels of side effects.

For detection of expression or activity of EGFR, a tissue (cancer tissue, blood vessel wall tissue, skin, oral mucosa etc.) or a body fluid (blood, lymph) and the like, which is obtained from patients, is applied to a test to detect expression or activity of EGFR. Such tests are known to those skilled in the art. With regard to the treatment of some conditions, for example, atherosclerosis, certain people may be identified as being at high risk, for example, due to genetic, environmental or historical factors. Compounds within the scope of the present invention can be used in preventing or delaying the occurrence or reoccurrence of such conditions or otherwise treating the condition.

As mentioned above, the compounds of the present invention are effective in the treatment of cancer patients and also expected to be an agent for the prophylaxis and/or treatment of preventing transition from hormone sensitive cancer to resistant cancer in prostate cancer and breast cancer. Moreover, it is expected to an agent for the prophylaxis and/or treatment of angiogenesis associated with the growth of solid cancer and sarcoma, angiogenesis associated with cancer metastasis, angiogenesis associated with diabetic retinopathy, arteriosclerosis, psoriasis and the like.

The "overexpression or activation of EGFR" is an expression or activity not less than the expression amount or activity necessary for homeostasis of living organisms, and the expression or activity not less than the expression amount or activity necessary for normal tissue of the same origin.

The "patients showing overexpression or activation of EGFR" means the patients wherein EGFR is excessively expressed or activated, and preferably the patients wherein both are excessively expressed or activated. The EGFR inhibitor of the present invention is characterized by administration for the treatment of patients, wherein EGFR is excessively expressed or activated as mentioned above.

The "EGFR inhibitor" of the present invention is preferably a EGFR inhibitor to be administered to patients wherein EGFR is excessively expressed or activated. It is possible to use an EGFR inhibitor and another form of treatment simultaneously, separately or at time intervals. In other words, it is possible to administer an EGFR inhibitor and another drug or form of treatment simultaneously, separately or, for example, in a staggered manner in a single day or at given time intervals for several days to several weeks or several months, by various different routes.

The amount of compound administered will, of course, be dependent on the subject being treated, on the subject's weight, the severity of the affliction, the manner of administration and the judgment of the prescribing physician. However, to the extent that these compounds provide improved activity relative to other known small molecules in in vivo, in vitro, and animal studies, in the broadest sense, recommended dosages are those similar to those currently prescribed for other small molecules for this same purpose.

The therapy may be repeated intermittently while symptoms detectable or even when they are not detectable. The therapy may be provided alone or in combination with other drugs.

Preferably, a therapeutically effective dose of the compounds described herein will provide therapeutic benefit without causing substantial toxicity.

Toxicity of the compounds described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use human. The dosage of the compounds described lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fing1 et al., 1975, In: The Pharmacological Basis of Therapeutics, Ch.1, p.1). Preferred dosages range from 1 nM to 500 mM.

EXAMPLES

Experimental Methods

Example 1

Fluorescence Binding Assays

The compounds were tested for binding to the EGFR kinase by means of fluorescence spectroscopy as described in Yun, et al., "Structures of Lung Cander-derived EGFR Mutants and Inhibitor Complexes: Mechanism of Activation and Insights into Differential Inhibitor Sensitivity," *Cancer Cell*, 11:217-227 (2007), which is incorporated by reference herein in its entirety. The compounds were diluted to 10 μM in fluorescence buffer containing 20 mM Tris, 0.5% Glycerol, 250 mM NaCl, and 1 mM TCEP. The kinase domains were diluted to 50 nm in the same buffer. The buffer was degassed and aerated with nitrogen to remove dissolved oxygen. The assay was carried out on a Fluor® Max-2 fluorometer using a 1.0 cm path-length quartz cuvette with micro stirrer. The excitation and emission wavelengths were 285 nm and 340 nm, respectively. The compound solution was titrated into an aliquot of 2.5 ml kinase solution in the cuvette to obtain the indicated total concentration with a total volume increase of less than 200 μl. The emission fluorescence intensity was read 30 sec after addition of a compound, and the average of five measurements was recorded. A blank assay was performed in exactly the same manner except that the buffer without compound was used for the titration. Dissociation constants ($K_D$) were determined by nonlinear fitting of the fluorescence data using a modified static quenching model as described in Yun, et al., 2007. Representative results of testing are shown in FIG. 3.

Example 2

Effects of the Compounds on Cell Proliferation and Apoptosis

Tumor cell lines A549, Calu-3, NE91 and T6-17 were treated with the target compounds at various concentrations. HaSV-NIH cells was used as a control. Cell proliferation was assessed by the 3-(4,5-Dimethylthiazol-2-yl)-2,5-diphenyltetrazolium Bromide (MTT) assay 24 or 48 hours after treatment. Cell lines were plated in 96-well plates (4,000 cells/well) in DMEM with 10% FCS and various amounts of the CBM compounds or an irrelevant small molecule and incubated for 24 or 48 hours. MTT was added to the cells for 4 hours. Then cells were lysed in 50% SDS/20% dimethyl sulfoxide and kept at 37° C. overnight. Proliferation was assessed by optical density readings at 570 nm using a Tecan Spectra Fluor.

Apoptosis was analyzed by FACS analysis after Annexin V staining and propidium iodide staining of DNA, and by Western blotting tracking caspase cascade activation. Lung cancer cells NCI-H1666 and A549 were treated with a compound alone, Tarceva® alone or a combination of Tarceva® and the compound for 48 hours, stained and analyzed by FACS. To study caspase activation the cells was treated with combination of Tarceva® and activating compounds for 1, 4, 8 12 and 24 hours. The cell lysates were subjected to Western blotting with anti-caspase-8, anti-caspase-3, anti-caspase-9 and anti-PARP antibodies to detect cleavage. NCI-H1650 and H3255 cells expressing mutant EGFR were used as a positive control in the apoptosis studies.

Example 3

Inhibition of Anchorage-Independent Growth of EGFR-Transformed Cells

Studies on the effects of the target compounds on anchorage-independent growth of tumor cells used four different cell lines, A549, Calu-3, NE91 and T6-17, which have different levels of EGFR molecules on the cell surface. HaSV-NIH cells that do not express erbB receptor were used as a control. Cells were analyzed for their effects on anchorage-independent growth using soft agar assays described previously in Qian, et al., "Inhibition of p185neu kinase activity and cellular transformation of co-expression of a truncated neu protein," Oncogene, 13: 2149-2157 (1996). The cells were plated in triplicate in 0.4% agar-HBBS and allowed to grow for 2 to 3 weeks. The cells will be fed with 0.5 ml media containing compounds on the day after plating and once a week thereafter. The colonies were stained with the HBSS solution containing 1 mg/ml of P-iodonitrotetrazolium violet (2-[4-iodophenyl]-3-[4-nitrophenyl]-5-phenyltetrazolium chloride). The number of the colonies formed were counted.

Example 4

Effects of the Compounds on EGFR Phosphorylation, Downregulation and Downstream Signaling Pathways Studies measuring total EGFR phosphorylation and phosphorylation of different tyrosines, cell lines NE91, NCI-H1666 and A549 expressing wild type EGFR were treated with the target compounds for 3 hours followed by either induction with 50 ng/ml EGF for 15 min or no EGF induction. The cell lysates were subjected to the immunoprecipitation with anti-EGFR antibodies followed by Western blotting with anti-pY99 (total phospho-tyrosine), anti-pY845, anti-pY1045, anti-pY 1068 and/or anti-pY1173 antibodies.

Tumor cell lines A549, Calu-3, and NCI-H1666 were treated with the designed compounds alone, Tarceva® alone, or combination of the compound and Tarceva® at various concentrations. The cell lysates were subjected to Western blotting with either anti-phospho-Erk, the anti-phospho-Akt, or anti-phospho-STAT3 and anti-phospho-STAT5 antibodies. The total protein amount of Erk Akt, STAT3 and STAT5 protein was also examined by Western blot.

Since preliminary studies indicated that EGFR tyrosine kinase mutants exhibit hypophosphorylation at tyrosine residue 1045, hypoubiquitination, and impaired endocytosis, studies were done to determine if treatments with the compounds had similar effect. NE91 cells were treated with different concentrations of the compounds for 3 hours. The cell lysates were subjected to Western blotting with anti-phospho-tyrosine 1045 antibodies, or immunoprecipitation with anti-EGFR antibodies followed by Western blotting with anti-ubiquitin antibodies to detect the level of ubiquitination and anti-Cbl antibodies to detect binding of Cbl ubiquitin ligase to EGFR. The untereated NE91 lysate served as a negative control, while lysate of NR/Del cells was used as a positive control. EGFR degradation was studied by pulse-chase analysis. NE 91 cells was treated with 1 μM compounds for 3 hours, starved in DMEM lacking methionine and cysteine and metabolic labeled with a [35S]methionine-[35S]cysteine mixture. Cells were harvested at 0.5, 1, 2, 4 and 8 hours and lysed. EGFR were immunoprecipitated with anti-EGFR antibody, separated on SDS-PAGE gel, and analyzed by autoradiography.

Example 5

Enhancement of Tarceva®-Induced Inhibition of EGFR Phosphorylation in EGFR Expressing Tumor Cells The EGFR kinase assays to determine IC50 values were performed by Reaction Biology Corp. using HotSpot technology with the peptide substrate poly[Glu:Tyr] (4:1, 0.2 mg/ml) (http://www.reactionbiology.com). Kinase reactions were carried out in 20 mmol/L HEPES (pH 7.5), 10 mmol/L MgCl2, 1 mmol/L EGTA, 0.02% Brij 35, 0.02 mg/mL bovine serum albumin, 2 mmol/L DTT, and 1% DMSO. The final concentration of ATP was 10 µmol/L. Purified recombinant kinases were incubated with serial 3-fold dilutions of test compounds starting at a final concentration of 1 µmol/L. ATP concentration was 10 µmol/L. Dose response curves were fitted using Prism 5.0 from Graph-Pad Software.)

At the tested concentration of 20 µM, Tarceva® alone had an inhibitory effect on both cell lines (FIG. 4A and FIG. 4B; closed bars indicated as "Buffer"). Moreover, other cell lines that did not express EGFR (not shown) or expressed Her2/neu in its place were not markedly affected by these compounds. Since T6-17 cells do not express significant levels of EGFR, the small effect of Tarceva® on proliferation of this cell line (FIG. 4B) is probably non-specific. While the tested compounds significantly enhanced the inhibitory effect of Tarceva® on proliferation of the NE99 cells (FIG. 4A), they had no effect on the non-specific inhibition of T6-17 (EGFR negative) cells by Tarceva® (FIG. 4B).

Example 6

Effect of EEO3 and Tarceva® on EGFR Phosphorylation and Downstream Signaling

Figure 7A:
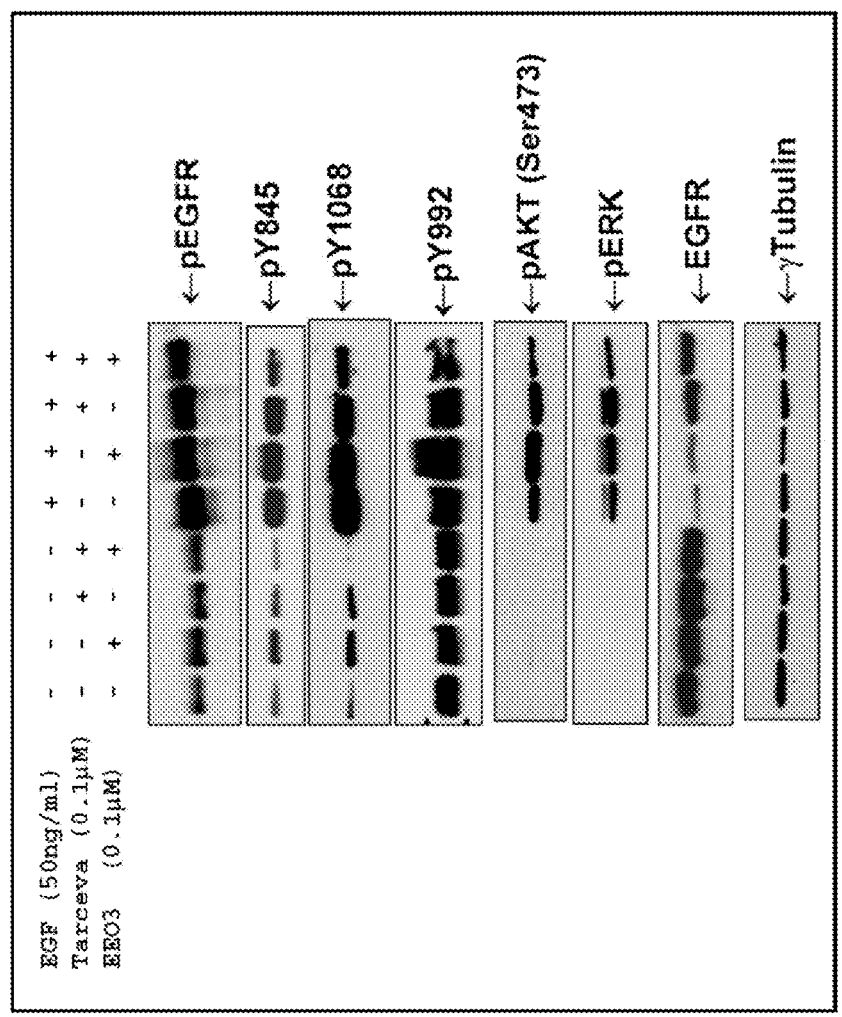
FIG. 7 shows two Western Blot analyses showing the effect of EEO3 and Tarceva® on EGFR phosphorylation and downstream signaling.
Figure 7B:
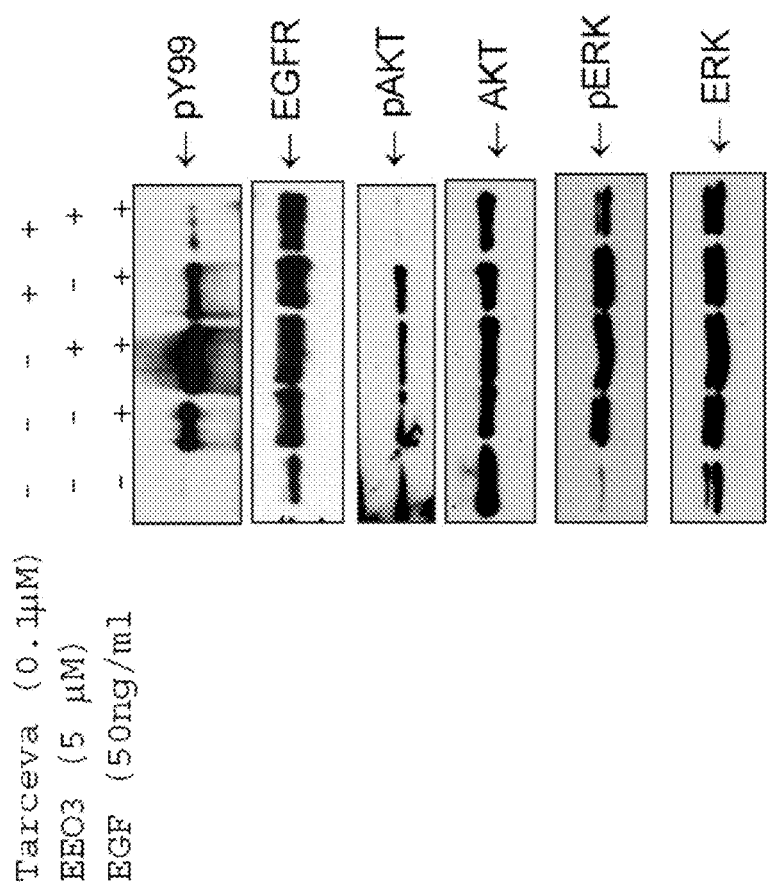

In separate experiments, NE91 cells (mouse fibroblasts over-expressing wild type human EGFR) and A549 human lung cancer cells were starved overnight, incubated with EEO3 (0.1 µM) (lanes 2, 6), Tarceva® (0.1 µM) (lanes 3, 7) or both (lanes 4, 8) for 1 hr, and harvested (lanes 1-4) or induced with EGF (50 ng/ml) for 15 minutes and harvested. Equal amounts of total protein were loaded on 10% SDS-PAGE gel, separated, transferred to a PVDF membrane, and probed with pY99, pERK, antibodies (Santa Cruz Biotechnology), or antibodies against specific phospho-tyrosines of EGFR (pY845, pY1068, pY992) or AKT phospho-serine (473) (Cell Signaling Technology). Total EGFR and γ-tubulin levels were determined as controls using the 1005 (Santa Cruz Biotechnology) and GTU88 (Sigma) Abs, respectively. The results are shown in FIG. 7A for the NE91 cells and FIG. 7B for the A549 cells.

Example 7

Effects of EEO3 and EEO4 on Tarceva®-Induced Inhibition of Cell Proliferation in Human Lung Cancer Cell Line A549

Figure 11:
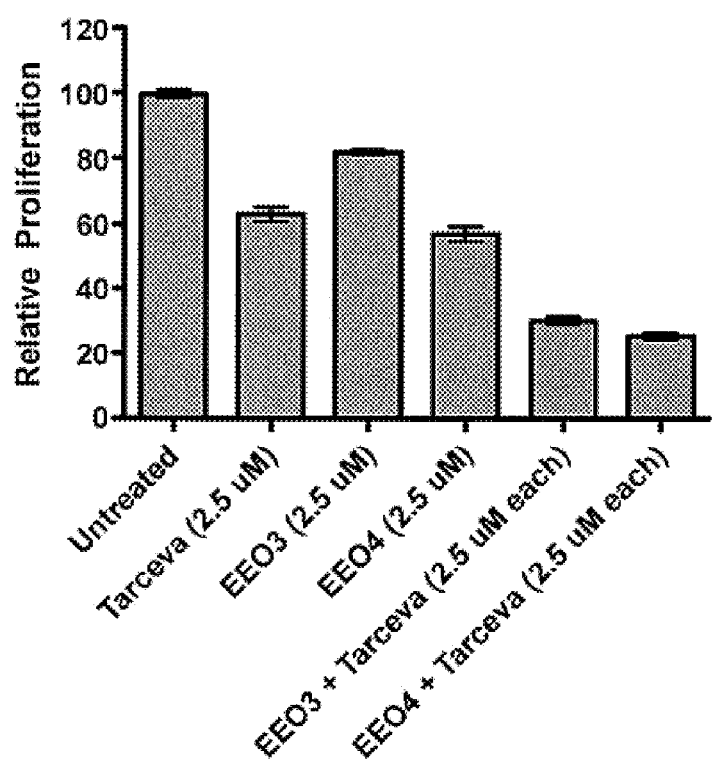
FIG. 11 shows the effects of EEO3 and EEO4 on Tarceva®-induced inhibition of cell proliferation in human lung cancer cell line A549.

5 mg/ml Poly(2-hydroxyethyl methacrylate) (PolyHEMA) powder (Sigma) in 95% ethanol was dissolved at 50 C, filtered, and 200 ul was pipeted into each well of 96-well flat-bottom plates. Plates were dried at 50 C overnight in a dry incubator. Wells were rinsed with PBS and pre-moistened with 50 ul of cell culture media. Six thousand cells were added per well. The compounds were added the following day to each well and the plates were incubated for 72 hrs in a humidified 37 C incubator with 5% CO2. Alamar blue (Serotec) indicator dye (7%) was added to each well and incubated for 2-4 hrs until the dye turned from blue to purple/red. A spectrophotometer (SPECTRA Fluor, Tecan) was used to measure the colorimetric dye at wavelengths of 530 nm (ex)/ 595 nm (em) and results were normalized to 100%. Bars represent mean (n=6)+/−SEM. See FIG. 11.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article.

The disclosures of each patent, patent application, and publication cited or described in this document are hereby incorporated herein by reference, in their entirety.

What is claimed:

1. A pharmaceutical composition comprising:
   (a) a compound of Formula (I) or Formula (II), or a pharmaceutically acceptable salt or prodrug thereof, in an amount effective to mimic an L858R mutation in a tyrosine kinase domain of a wild-type epidermal growth factor receptor (EGFR)

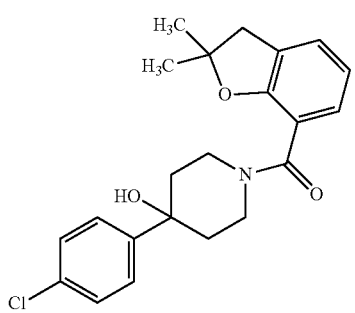

(b) an EGFR tyrosine kinase inhibitor in an amount effective to inhibit a cell proliferative disorder characterized by over-activity or overexpression of the EGFR; and
   (c) a pharmaceutically acceptable carrier, diluent, excipient or auxiliary.

2. The pharmaceutical composition of claim 1, wherein the tyrosine kinase inhibitor is erlotinib, gefitinib, or lapatinib.

3. A method of treating cancer comprising administering a pharmaceutically effective amount of the pharmaceutical composition of claim 1 to a patient in need of such treatment.

4. The method of claim 3, wherein the cancer affects an anus, breast, colon, prostate, lung, pancreas, ovary, or stomach.

5. The method of claim 3, wherein the patient is a human.

6. The method of claim 3, wherein the pharmaceutical composition of claim 1 is administered in conjunction with performing a non-drug therapy to the patient.

7. The method of claim 6, wherein the non-drug therapy is surgery, hypertensive chemotherapy, gene therapy, thermotherapy, cryotherapy, photodynamic therapy, laser cauterization, radiotherapy, or a combination thereof.

8. The method of claim 3, wherein the tyrosine kinase inhibitor is erlotinib, gefitinib, or lapatinib.

9. The pharmaceutical composition of claim 1, formulated in a dosage form suitable for oral, rectal, sub-lingual, mucosal, nasal, ophthalmic, subcutaneous, intramuscular, intravenous, transdermal, spinal, intrathecal, intra-articular, intra-arterial, sub-arachnoid, bronchial, lymphatic, or intra-uterine administration.

10. The pharmaceutical composition of claim 1, formulated in a dosage form suitable for oral administration.

11. The pharmaceutical composition of claim 1 wherein the compound of Formula (I) or Formula (II) is a compound having the structure of Formula (I):

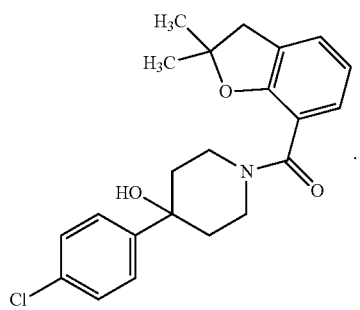

(I)

12. A method of treating cancer, comprising the step of administering the pharmaceutical composition of claim 1 to a patient in need of such treatment, wherein the compound of Formula (I) or Formula (II) is a compound having the structure of Formula (I):

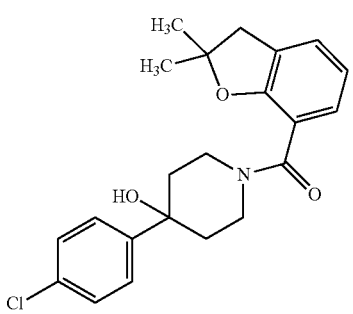

(I)

13. The method of claim 12, wherein the cancer is cancer of the anus, breast, colon, prostate, lung, pancreas, ovary, or stomach.

14. The method of claim 13, wherein the patient is a human.

15. The method of claim 14, wherein the pharmaceutical composition is administered in in conjunction with performing a non-drug therapy to the patient.

16. The method of claim 15, wherein the non-drug therapy is surgery, hypertensive chemotherapy, gene therapy, thermotherapy, cryotherapy, photodynamic therapy, laser cauterization, radiotherapy, or a combination thereof.

17. The method of claim 12, wherein the tyrosine kinase inhibitor is erlotinib, gefitinib, or lapatinib.

18. The pharmaceutical composition of claim 11, wherein the tyrosine kinase inhibitor is erlotinib, gefitinib, or lapatinib.

19. The pharmaceutical composition of claim 12, formulated in a dosage form suitable for oral, rectal, sub-lingual, mucosal, nasal, ophthalmic, subcutaneous, intramuscular, intravenous, transdermal, spinal, intrathecal, intra-articular, intra-arterial, sub-arachnoid, bronchial, lymphatic, or intra-uterine administration.

20. The pharmaceutical composition of claim 1 wherein the compound of Formula (I) or Formula (II) is a compound having the structure of Formula (II):

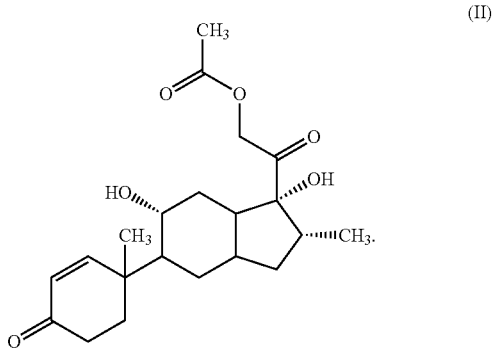 [SMILES: CC(=O)OCC(=O)[C@]1(O)C2C[C@@H](O)C(C3(C)C=CC(=O)CC3)CC2C[C@H]1C]

(II)

21. The pharmaceutical composition of claim 20, wherein the tyrosine kinase inhibitor is erlotinib, gefitinib, or lapatinib.

22. The pharmaceutical composition of claim 21, formulated in a dosage form suitable for oral, rectal, sub-lingual, mucosal, nasal, ophthalmic, subcutaneous, intramuscular, intravenous, transdermal, spinal, intrathecal, intra-articular, intra-arterial, sub-arachnoid, bronchial, lymphatic, or intra-uterine administration.

23. A method of treating cancer, comprising the step of administering a pharmaceutical composition of claim 20 to a patient in need of such treatment.

24. The method of claim 22, wherein the cancer is cancer of the anus, breast, colon, prostate, lung, pancreas, ovary, or stomach.

25. The method of claim 23, wherein the tyrosine kinase inhibitor is erlotinib, gefitinib, or lapatinib.

26. A pharmaceutical composition comprising:
(a) a compound capable of mimicking the L858R mutation in the tyrosine kinase domain of wild-type epidermal growth factor receptor (EGFR), in an amount effective to mimic the L858R mutation in the tyrosine kinase domain of the wild-type epidermal growth factor receptor (EGFR), (b) an EGFR tyrosine kinase inhibitor in an amount effective to inhibit a cell proliferative disorder characterized by over-activity or overexpression of the EGFR; and
(c) a pharmaceutically acceptable carrier, diluent, excipient or auxiliary, wherein the compound capable of mimicking the L858R mutation has a structure of any one of Formulae III-V:

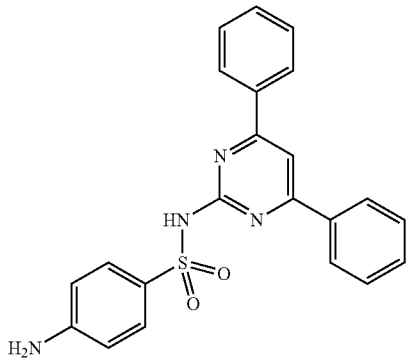
(III)

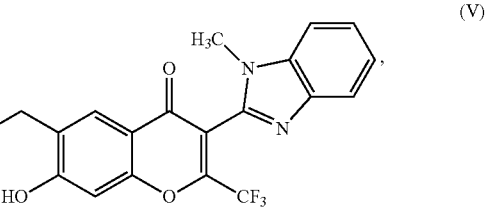
(IV)

(V)

or a pharmaceutically acceptable salt or prodrug thereof.

27. The pharmaceutical composition of claim 26, formulated in a dosage form suitable for oral, rectal, sub-lingual, mucosal, nasal, ophthalmic, subcutaneous, intramuscular, intravenous, spinal, intrathecal, intra-articular, intra-arterial, sub-arachinoid, bronchial, lymphatic, or intra-uterine administration.

\* \* \* \* \*

SEQUENCE LISTING

```
<160> NUMBER OF SEQ ID NOS: 3

<210> SEQ ID NO 1
<211> LENGTH: 984
<212> TYPE: DNA
<213> ORGANISM: Homo sapiens
<220> FEATURE:
<221> NAME/KEY: CDS
<222> LOCATION: (1)..(984)

<400> SEQUENCE: 1 agt gga gaa gct ccc aac caa gct ctc ttg agg atc ttg aag gaa act      48
Ser Gly Glu Ala Pro Asn Gln Ala Leu Leu Arg Ile Leu Lys Glu Thr
1               5                  10                  15 gaa ttc aaa aag atc aaa gtg ctg ggc tcc ggt gcg ttc ggc acg gtg      96
Glu Phe Lys Lys Ile Lys Val Leu Gly Ser Gly Ala Phe Gly Thr Val
            20                  25                  30 tat aag gga ctc tgg atc cca gaa ggt gag aaa gtt aaa att ccc gtc     144
Tyr Lys Gly Leu Trp Ile Pro Glu Gly Glu Lys Val Lys Ile Pro Val
        35                  40                  45 gct atc aag gaa tta aga gaa gca aca tct ccg aaa gcc aac aag gaa     192
Ala Ile Lys Glu Leu Arg Glu Ala Thr Ser Pro Lys Ala Asn Lys Glu
    50                  55                  60 atc ctc gat gaa gcc tac gtg atg gcc agc gtg gac aac ccc cac gtg     240
```

```
Ile Leu Asp Glu Ala Tyr Val Met Ala Ser Val Asp Asn Pro His Val
 65                  70                  75                  80 tgc cgc ctg ctg ggc atc tgc ctc acc tcc acc gtg cag ctc atc acg          288
Cys Arg Leu Leu Gly Ile Cys Leu Thr Ser Thr Val Gln Leu Ile Thr
                     85                  90                  95 cag ctc atg ccc ttc ggc tgc ctc ctg gac tat gtc cgg gaa cac aaa          336
Gln Leu Met Pro Phe Gly Cys Leu Leu Asp Tyr Val Arg Glu His Lys
                100                 105                 110 gac aat att ggc tcc cag tac ctg ctc aac tgg tgt gtg cag atc gca          384
Asp Asn Ile Gly Ser Gln Tyr Leu Leu Asn Trp Cys Val Gln Ile Ala
            115                 120                 125 aag ggc atg aac tac ttg gag gac cgt cgc ttg gtg cac cgc gac ctg          432
Lys Gly Met Asn Tyr Leu Glu Asp Arg Arg Leu Val His Arg Asp Leu
        130                 135                 140 gca gcc agg aac gta ctg gtg aaa aca ccg cag cat gtc aag atc aca          480
Ala Ala Arg Asn Val Leu Val Lys Thr Pro Gln His Val Lys Ile Thr
145                 150                 155                 160 gat ttt ggg ctg gcc aaa ctg ctg ggt gcg gaa gag aaa gaa tac cat          528
Asp Phe Gly Leu Ala Lys Leu Leu Gly Ala Glu Glu Lys Glu Tyr His
                165                 170                 175 gca gaa gga ggc aaa gtg cct atc aag tgg atg gca ttg gaa tca att          576
Ala Glu Gly Gly Lys Val Pro Ile Lys Trp Met Ala Leu Glu Ser Ile
                180                 185                 190 tta cac aga atc tat acc cac cag agt gat gtc tgg agc tac ggg gtg          624
Leu His Arg Ile Tyr Thr His Gln Ser Asp Val Trp Ser Tyr Gly Val
            195                 200                 205 acc gtt tgg gag ttg atg acc ttt gga tcc aag cca tat gac gga atc          672
Thr Val Trp Glu Leu Met Thr Phe Gly Ser Lys Pro Tyr Asp Gly Ile
        210                 215                 220 cct gcc agc gag atc tcc tcc atc ctg gag aaa gga gaa cgc ctc cct          720
Pro Ala Ser Glu Ile Ser Ser Ile Leu Glu Lys Gly Glu Arg Leu Pro
225                 230                 235                 240 cag cca ccc ata tgt acc atc gat gtc tac atg atc atg gtc aag tgc          768
Gln Pro Pro Ile Cys Thr Ile Asp Val Tyr Met Ile Met Val Lys Cys
                245                 250                 255 tgg atg ata gac gca gat agt cgc cca aag ttc cgt gag ttg atc atc          816
Trp Met Ile Asp Ala Asp Ser Arg Pro Lys Phe Arg Glu Leu Ile Ile
                260                 265                 270 gaa ttc tcc aaa atg gcc cga gac ccc cag cgc tac ctt gtc att cag          864
Glu Phe Ser Lys Met Ala Arg Asp Pro Gln Arg Tyr Leu Val Ile Gln
            275                 280                 285 ggg gat gaa aga atg cat ttg cca agt cct aca gac tcc aac ttc tac          912
Gly Asp Glu Arg Met His Leu Pro Ser Pro Thr Asp Ser Asn Phe Tyr
        290                 295                 300 cgt gcc ctg atg gat gaa gaa gac atg gac gac gtg gtg gat gcc gac          960
Arg Ala Leu Met Asp Glu Glu Asp Met Asp Asp Val Val Asp Ala Asp
305                 310                 315                 320 gag tac ctc atc cca cag cag ggc                                          984
Glu Tyr Leu Ile Pro Gln Gln Gly
                325

<210> SEQ ID NO 2
<211> LENGTH: 328
<212> TYPE: PRT
<213> ORGANISM: Homo sapiens

<400> SEQUENCE: 2

Ser Gly Glu Ala Pro Asn Gln Ala Leu Leu Arg Ile Leu Lys Glu Thr
 1                   5                  10                  15

Glu Phe Lys Lys Ile Lys Val Leu Gly Ser Gly Ala Phe Gly Thr Val
```

```
            20                  25                  30
Tyr Lys Gly Leu Trp Ile Pro Glu Gly Glu Lys Val Lys Ile Pro Val
            35                  40                  45

Ala Ile Lys Glu Leu Arg Glu Ala Thr Ser Pro Lys Ala Asn Lys Glu
 50                  55                  60

Ile Leu Asp Glu Ala Tyr Val Met Ala Ser Val Asp Asn Pro His Val
 65                  70                  75                  80

Cys Arg Leu Leu Gly Ile Cys Leu Thr Ser Thr Val Gln Leu Ile Thr
                 85                  90                  95

Gln Leu Met Pro Phe Gly Cys Leu Leu Asp Tyr Val Arg Glu His Lys
            100                 105                 110

Asp Asn Ile Gly Ser Gln Tyr Leu Leu Asn Trp Cys Val Gln Ile Ala
            115                 120                 125

Lys Gly Met Asn Tyr Leu Glu Asp Arg Arg Leu Val His Arg Asp Leu
            130                 135                 140

Ala Ala Arg Asn Val Leu Val Lys Thr Pro Gln His Val Lys Ile Thr
145                 150                 155                 160

Asp Phe Gly Leu Ala Lys Leu Leu Gly Ala Glu Glu Lys Glu Tyr His
                165                 170                 175

Ala Glu Gly Gly Lys Val Pro Ile Lys Trp Met Ala Leu Glu Ser Ile
            180                 185                 190

Leu His Arg Ile Tyr Thr His Gln Ser Asp Val Trp Ser Tyr Gly Val
            195                 200                 205

Thr Val Trp Glu Leu Met Thr Phe Gly Ser Lys Pro Tyr Asp Gly Ile
            210                 215                 220

Pro Ala Ser Glu Ile Ser Ser Ile Leu Glu Lys Gly Glu Arg Leu Pro
225                 230                 235                 240

Gln Pro Pro Ile Cys Thr Ile Asp Val Tyr Met Ile Met Val Lys Cys
                245                 250                 255

Trp Met Ile Asp Ala Asp Ser Arg Pro Lys Phe Arg Glu Leu Ile Ile
            260                 265                 270

Glu Phe Ser Lys Met Ala Arg Asp Pro Gln Arg Tyr Leu Val Ile Gln
            275                 280                 285

Gly Asp Glu Arg Met His Leu Pro Ser Pro Thr Asp Ser Asn Phe Tyr
            290                 295                 300

Arg Ala Leu Met Asp Glu Asp Met Asp Asp Val Val Asp Ala Asp
305                 310                 315                 320

Glu Tyr Leu Ile Pro Gln Gln Gly
                325

<210> SEQ ID NO 3
<211> LENGTH: 328
<212> TYPE: PRT
<213> ORGANISM: Homo sapiens

<400> SEQUENCE: 3

Ser Gly Glu Ala Pro Asn Gln Ala Leu Leu Arg Ile Leu Lys Glu Thr
1               5                   10                  15

Glu Phe Lys Lys Ile Lys Val Leu Gly Ser Gly Ala Phe Gly Thr Val
            20                  25                  30

Tyr Lys Gly Leu Trp Ile Pro Glu Gly Glu Lys Val Lys Ile Pro Val
            35                  40                  45

Ala Ile Lys Glu Leu Arg Glu Ala Thr Ser Pro Lys Ala Asn Lys Glu
 50                  55                  60
```

```
Ile Leu Asp Glu Ala Tyr Val Met Ala Ser Val Asp Asn Pro His Val
65                  70                  75                  80

Cys Arg Leu Leu Gly Ile Cys Leu Thr Ser Thr Val Gln Leu Ile Thr
                85                  90                  95

Gln Leu Met Pro Phe Gly Cys Leu Leu Asp Tyr Val Arg Glu His Lys
            100                 105                 110

Asp Asn Ile Gly Ser Gln Tyr Leu Leu Asn Trp Cys Val Gln Ile Ala
            115                 120                 125

Lys Gly Met Asn Tyr Leu Glu Asp Arg Arg Leu Val His Arg Asp Leu
            130                 135                 140

Ala Ala Arg Asn Val Leu Val Lys Thr Pro Gln His Val Lys Ile Thr
145                 150                 155                 160

Asp Phe Gly Arg Ala Lys Leu Leu Gly Ala Glu Glu Lys Glu Tyr His
            165                 170                 175

Ala Glu Gly Gly Lys Val Pro Ile Lys Trp Met Ala Leu Glu Ser Ile
            180                 185                 190

Leu His Arg Ile Tyr Thr His Gln Ser Asp Val Trp Ser Tyr Gly Val
            195                 200                 205

Thr Val Trp Glu Leu Met Thr Phe Gly Ser Lys Pro Tyr Asp Gly Ile
210                 215                 220

Pro Ala Ser Glu Ile Ser Ser Ile Leu Glu Lys Gly Glu Arg Leu Pro
225                 230                 235                 240

Gln Pro Pro Ile Cys Thr Ile Asp Val Tyr Met Ile Met Val Lys Cys
            245                 250                 255

Trp Met Ile Asp Ala Asp Ser Arg Pro Lys Phe Arg Glu Leu Ile Ile
            260                 265                 270

Glu Phe Ser Lys Met Ala Arg Asp Pro Gln Arg Tyr Leu Val Ile Gln
            275                 280                 285

Gly Asp Glu Arg Met His Leu Pro Ser Pro Thr Asp Ser Asn Phe Tyr
            290                 295                 300

Arg Ala Leu Met Asp Glu Glu Asp Met Asp Asp Val Val Asp Ala Asp
305                 310                 315                 320

Glu Tyr Leu Ile Pro Gln Gln Gly
                325
```